United States Patent [19]

O'Hara

[11] Patent Number: 5,414,076
[45] Date of Patent: May 9, 1995

[54] DNA ENCODING GIBBON APE LEUKEMIA VIRUS RECEPTOR

[75] Inventor: Bryan M. O'Hara, Pearl River, N.Y.

[73] Assignee: American Cyanamid Company, Wayne, N.J.

[21] Appl. No.: 674,287

[22] Filed: Mar. 25, 1991

Related U.S. Application Data

[63] Continuation-in-part of Ser. No. 398,351, Aug. 24, 1989, abandoned.

[51] Int. Cl.⁶ .................. C07H 15/12; C07K 15/00
[52] U.S. Cl. .................. 536/23.5; 530/350; 530/324; 530/325; 530/326; 530/327; 530/328; 530/329
[58] Field of Search ............ 530/350, 326, 324, 325, 530/329, 327, 328; 536/23.5

[56] References Cited

U.S. PATENT DOCUMENTS 5,151,361 9/1992 O'Hara ...................... 435/240.2

OTHER PUBLICATIONS

Sommerfelt et al. *Virology* 176:58–69 (1990).
Kaelbling et al. *J. of Virology* 65(4):1743–1747 (1991).
Adamson et al. *Virology* 183: 778–781 (1991).
Takeuchi et al. *J. of Virology* 66(2):1219–1222 (1992).
Johann et al. *J. of Virology* 66(3):1635–1640 (1992).
O'Hara et al. *Cell Growth & Differentiation* 1(3):119 (1990).

*Primary Examiner*—Robert J. Hill, Jr.
*Assistant Examiner*—Shelly Guest Cermale
*Attorney, Agent, or Firm*—James J. Harrington

[57] ABSTRACT

The present invention relates to the gibbon ape leukemia virus (GALV) receptor protein and gene, as well as methods for regulating viral entry into cells.

2 Claims, 18 Drawing Sheets

```
  1 GAGCTGTCCCCGGTGCCGCCGGACCCGGCCGTGCCGTGTGCCGTGGCTC   50
 51 CAGCCGCTGCCGCCTCGATCCTCCTCCGTCCTCCCGCTCCCGCCCTTTC  100
101 CCTGGATGAACTTGCGTCCTTCTCTCCGCCATGGAATTCTGCTCCG     150
151 TGCTTTTAGCCCTCCTGAGCCAAAGAACCCAGACAACAGATGCCCATA   200
201 CGCAGCGTATAGCAGTAACTCCCCAGCTCGGTTCTGTGCCGTAGTTTAC  250
251 AGTATTTAATTTTATAATATATATTATTATTATAGCATTTTGATAC     300
301 CTCATATTCTGTTTACACATTCTTGAAAGGCGCTCAGTAGTTCTCTTACTA 350
351 AACAACCACTACTCCAGAGAATGGCAACGCTGATTACCAGTACTACAGCT 400
401 GCTACCGCGCTTCTGGTGTCCTTTGGTGGACTACCTATGGATGCTCATCCT 450
451 GGGCTTCATTATTGCATTTGTCTTGGCATTCTCCGTGGGAGCCAATGATG 500
501 TAGCAAATTCTTTTTGGTACAGCTGTGGGCTCAGTGTAGTGACCCTGAAG 550
551 CAAGCCTGCATCCTAGCTAGCATCTTGAAACAGTGGGCTCTGTCTTACT  600
601 GGGGGCCAAAGTGAGCGAAGCCATCCGGAAGGGCTTGATTGACGTGGAGA 650
651 TGTACAACTCGACTCGTGTGCTACTCGTCGGCTGGCTTCGTTTTGAAGCTCCCTATG 700
701 TTTGGTTCTGCTGTGTGGGCAACTCGTGGCTTCGTTTTGAAGCTCCCTAT 750
751 TTCTGGAACCCATTGTATTGTTGGTGCAACTATTGGTTCTCCCTCGTGG  800
801 CAAAGGGCAGGAGGGTGTCAAGTGGTCTGAACTGGTCTGATAAAATTGTGATG 850
851 TCTTGGTTCGTGTCCCCACTGCTTTCTCGGAATTATGTCTGGAATTTTATT 900
901 CTTCCTGGTTCGTGCATTCATCCTCCATAAGGCAGATCCAGTTCCTAATG 950
951 GTTTGCGAGCTTTGCCAGTTTTCTATGCCTGCACAGTTGGAATAAACCTC 1000
```

FIG. 6A

```
 1001 ----,----+----,----+----,----+----,----+----,----+----,----+
      TTTCCATCATGTATACTGGAGCACCGTTGCTGGCTTTGACAAACTTCC  1050
 1051 TCTGTGGGTACCATCCTCATTCGGTGGATGTGCAGTTTTCTGTGCCC  1100
 1101 TTATCGTCTGGTTCTTTGTATGTCCCAGGATGAAGAGAAATTGAACGA  1150
 1151 GAAATAAAGTGTAGTCCTTCTGAAAGCCCCTAATGGAAAAAAGAATAG  1200
 1201 CTTGAAAGAAGACCATGAAGAAACAAAGTTGTCTCTGTTGGTGATATTGAAA  1250
      ----,----+----,----+----,----+----,----+----,----+----,----+
 1251 ACAAGCATCCTGTTTCTGAGGTAGGCCTGCCACTGTGCCCCTCCAGGCT  1300
 1301 GTGGTGGAGGAGAGAGAACAGTCTCATTCAAACTTGGAGATTGGAGGAAGC  1350
 1351 TCCAGAGAGAGAGAGGCTTCCCAGCGTGGACTTGAAAGAGGAAACCAGCA  1400
 1401 TAGATAGCACCGTGAATGGTGCAGTGCAGTTGCCTAATGGAACCTTGTC  1450
 1451 CAGTTCAGTCAAGCCGTCAGCAACCAAATAAACTCCAGTGGCCACTCCCA  1500
      ----,----+----,----+----,----+----,----+----,----+----,----+
 1501 GTATCACACCGTGCATAAGGATTCCGGCCTGTACAAAGAGCTACTCCATA  1550
 1551 AATTACATCTTGCCAAGGTGGGAGATTGCAGGTGGGAGACTCCGGTGACAAA  1600
 1601 CCCTTAAGGCGCAATAATAGCTATACTTCCTATACCATGCAATATGTGG  1650
 1651 CATGCCCTCTGATTCATTCCGTGCCAAAGAAGGTGAACAGAAGGGCGAAG  1700
 1701 AAATGGAGAAGCTGACATGGCCTAATGCCAGACTCCAAGAAGCGAATTCGA  1750
      ----,----+----,----+----,----+----,----+----,----+----,----+
 1751 ATGGACAGTTACACCAGTTACTGCAATGCTGTGTCTGACCTTCACTCAGC  1800
 1801 ATCTGAGATAGACATGAGTCAAGGCAGCGATGGTCTAGGTGACAGAA  1850
 1851 AAGGAAGTAATGGCTCTCTAGAAGAATGGTATGACCAGGATAAGCCTGAA  1900
 1901 GTCTCTCCTCTTCCCAGTTCCTGCAGATCCTTACAGCCTGCTTTGGGTC  1950
 1951 ATTCGCCCATGGTGGCAATGACGTAAGCAATGCCATTGGGCCTCTGGTTG  2000
      ----,----+----,----+----,----+----,----+----,----+----,----+
 2001 CTTTATATTGGTTTATGACACAGGAGATGTTTCTTCAAAAGTGGCAACA  2050
 2051 CCAATATGGCTTCTCACTCTATGGTGGTGTTGGTATCTGTGTTGGTCTGTG  2100
 2101 GGTTTGGGAAGAAGAGTTATCCAGACACCATGGGGAAGGATCTGACACCGA  2150
 2151 TCACACCCTCTAGTGGCTTCAGTATTGAACTGGCATCTGCCCTCACTGTG  2200
 2201 GTGATTGCATCAAATATTGGCCTTCCCATCCAGTACAACACATTGTAAAGT  2250
```

FIG.6B

```
2251  GGGCTCTGTGTGTCTGTTGTTGGCTGTGGCTCCGGTCCGGTCCAAGAAGGCTGTTGACT  2300
2301  GGCGTCTCTTCGTAACATTTTATGGCCTGGTTGTCACAGTCCCCATT              2350
2351  TCTGGAGTTATCAGTGCTGCTGCCATCATGGCAATCTTCAGATATGTCATCCT        2400
2401  CAGAATGTGAAGCTGTTTGAGATTAAAATTTGTGTCAATGTTTGGGACCA           2450
2451  TCTTAGGTATTCCTGCTCCCCTGAAGAATGATTACAGTGTTAACAGAAGA           2500

2501  CTGACAAGAGTCTTTTTATTTGGGAGCAGAGGAGGAAGTGTTACTTGTG            2550
2551  CTATAACTGCTTTTGTGCTAAATATGAATTGTCTCAAAATTAGCTGTGTA           2600
2601  AAATAGCCCGGGTTCCACTGGCTCCTGCTGAGGTCCCCTTTCCTTCTGGG           2650
2651  CTGTGAATTCCTGTACATATTCTCTACTTTTGTATCAGGCTTCAATTC             2700
2701  CATTATGTTTTAATGTTTGTCTCTGAAGATGACTTGTGATTTTTTTTCTT           2750

2751  TTTTTTAAACCATGAAGAGCCGTTTGACAGAGCCATGCTCTGCGTTGTTGG          2800
2801  TTTCACCAGCTTCTGCCCTGCACATGCACAGGATTAACAACAAAAATAT            2850
2851  AACTACAACTTCCCTTGTAGTCTTATATAAGTAGAGTCCTTGGTACTC             2900
2901  TGCCCTCCTGTCAGTAGTGGCAGGATCTATTGGCATATTCGGGAGCTTCT           2950
2951  TAGAGGGATGAGGTTCTTTGAACACAGTGAAAATTTAAATTAGTAACTTT           3000

3001  TTTGCAAGCAGTTTATTGACTGTTATTGCTAAGAAGAAGTAAGAAAGAAA           3050
3051  AAGCCTGTTGGCAATCTTGGTTATTCTTTAAGATTTCTGGCAGTGTGGG            3100
3101  ATGGATGAATGAAGTGGAATGTGAACTTTGGGCAAGTAAATGGGACAGC            3150
3151  CTTCCATGTTCATTTGTCTACCTCTTAACTGAATAAAAAGCCTACAGTT            3200
3201  TTTAGAAAAAA                                                   3220
```

```
                                                                              -
  1 Met Ala -   Leu Ile -   Ser Thr -   Thr Ala -   Ala Ser           15
 16 Gly Pro     Val Asp     Leu Trp     Met Leu     Gly Phe Ile       30
 31 Ile Ala     Phe Leu     Phe Ser     Val Gly     Ala Val Ala       45
 46 Asn Ser     Gly Thr     Ala Val     Gly Ser     Asp Val Lys       60
 61 Gln Ala -   Cys Ile -   Leu Ala -   Ser Ile -   Phe Gly Thr -   Val Gly Ser Val   75
 76 Leu Leu     Gly Ala     Lys Val     Ser Glu     Thr Ala     Lys Gly Leu Ile       90
 91 Asp Val     Glu Met     Tyr Asn     Ser Thr     Gln Gly     Leu Leu Met Ala Gly  105
106 Ser Val     Ser Ala     Met Phe     Gly Ser     Ala Val     Trp Gln Leu Val Ala  120
121 Ser Phe     Leu Lys     Leu Pro     Ile Ser     Gly Thr     His Cys Ile Val Gly  135
136 Ala Thr -   Ile Gly -   Phe Ser -   Leu Val -   Ala Lys -   Gly Gln Gly Val     150
151 Lys Trp     Ser Glu     Leu Ile     Lys Val     Met Ser     Trp Phe Val Ser      165
166 Pro Leu     Leu Ser     Gly Ile     Met Ser     Gly Ile     Leu Phe Phe Leu Val  180
181 Arg Ala     Phe Ile     Leu His     Lys Ala     Asp Pro     Val Pro Asn Gly Leu  195
196 Arg Ala     Leu Pro     Val Phe     Tyr Ala     Cys Thr     Gly Ile Asn Leu      210
211 Phe Ser -   Ile Met -   Tyr Thr -   Gly Ala -   Pro Leu -   Leu Gly Phe Asp Lys  225
226 Leu Pro     Trp Gly     Thr Ile     Leu Ile     Ser Val     Gly Cys Ala Val      240
241 Phe Cys     Ala Leu     Val Trp     Phe Phe     Val Cys     Pro Arg Met Lys      255
256 Arg Lys     Ile Glu     Arg Glu     Lys Ile     Cys Ser     Ser Pro Ser Glu Pro  270
271 Leu Met     Glu Lys     Lys Asn     Ser Leu     Lys Lys     Glu Asp His Glu Thr  285
286 Lys Leu     Val Gly     Asp Ile     Glu Asn     Ser Ile     Glu Asn Lys His Pro Val Ser Glu  300
```

FIG. 7B

```
301 Val Gly Pro Ala Thr Val Pro Leu Gln Ala Val Val Glu Arg 315
316 Thr Val Ser Phe Lys Leu Asp Leu Glu Glu Ala Pro Glu Arg 330
331 Glu Arg Leu Pro Ser Val Asp Lys Glu Glu Thr Ser Ile Asp 345
346 Ser Thr Val Asn Gly Ala Val Gln Leu Pro Asn Gly Asn Leu Val 360
361 Gln Phe Ser Gln Ala Val Ser Asn Ile Asn Ser Ser Gly His 375

376 Ser Gln Tyr His Thr Val His Lys Asp Ser Gly Leu Tyr Lys Glu 390
391 Leu Leu His Lys Leu His Leu Ala Lys Val Gly Asp Cys Met Gly 405
406 Asp Ser Gly Asp Lys Pro Arg Arg Asn Ser Asn Ser Tyr Thr Ser 420
421 Tyr Thr Met Ala Ile Cys Gly Met Pro Leu Asp Ser Phe Arg Ala 435
436 Lys Glu Gly Gln Lys Gly Gly Met Glu Asp Lys Lys Leu Thr Trp 450

451 Pro Asn Ala Asp Ser Lys Arg Ile Arg Met Asp Ser Tyr Thr 465
466 Ser Tyr Cys Asn Ala Val Ser Asp Leu His Ser Ala Ser Glu Ile 480
481 Asp Met Ser Val Lys Ala Ala Met Gly Leu Asp Arg Lys Gly 495
496 Ser Asn Gly Ser Leu Glu Glu Trp Tyr Gln Asn Asp Lys Pro Glu 510
511 Val Ser Leu Leu Phe Gln Phe Leu Ile Leu Thr Ala Cys Phe 525

526 Gly Ser Phe Ala His Gly Gly Asn Asp Val Ser Asn Ala Ile Gly 540
541 Pro Leu Val Ala Leu Tyr Leu Val Tyr Asp Thr Gly Asp Val Ser 555
556 Ser Lys Val Ala Thr Pro Ile Trp Leu Leu Tyr Gly Gly Val 570
571 Gly Ile Cys Val Gly Leu Trp Val Trp Gly Arg Arg Val Ile Gln 585
586 Thr Met Gly Lys Asp Leu Thr Pro Ile Thr Pro Ser Glu Gly Phe 600

601 Ser Ile Glu Leu Ala Ser Ala Leu Thr Val Ile Ala Ser Asn 615
616 Ile Gly Leu Pro Ile Ser Thr Thr His Cys Lys Val Gly Ser Val 630
631 Val Ser Val Gly Trp Leu Arg Ser Lys Lys Ala Val Asp Trp Arg 645
646 Leu Phe Arg Asn Ile Phe Met Ala Trp Phe Val Thr Pro Ile 660
661 Ser Gly Val Ile Ser Ala Ala Ile Phe Arg Tyr Val 675

676 Ile Leu Arg Met Ter 680
```

```
   1  GACGGTATCGATAAGCTTGATATCGAATTCCCTGTGCTCCACCTTGCACAGCGTTTGGGG    60
  61  GACTGAAGACATAAGTGACGGCGGGGGGGGGGGGACTATGCGGAGTCCCAGGCTGCCC    120
 121  TCTTCCCAGAGATGCGCCGCTATTGTTATTTTCTTCCACTTCGTCCCCCCAGGATGAACT   180
 181  TGCGTCCTTTCTCTAATCCGCCATGGAATTCTGCTCCGTGCTTTTAGCCCTCCAGAGCCA   240
 241  AAGAAACCCCAGACAACAGACGCCCAGACGCAGCAGCGTATAGCAGTAACTCCCCAGCTC   300
     ----+----+----+----+----+----+----+----+----+----+----+----+
 301  GGTTTCCGTGCCGTAGTTTACAGTATTTAATTTTATATAATATATACTATTTATTATAGC   360
 361  ATTTTGATACCTCATTCCGTTTACACATCTCAAAAGCCGCTTAGTAATTCTCTTATTATT   420
 421  TAAAGAACCACTACACTAGAGAATGGAATCTACTGTGGCAACGATTACTAGTACCCTAGC   480
 481  TGCTGTTACTGCTTCCGCTCCACCGAAGTATGACAATCTATGGATGCTCATCCTGGGCTT   540
 541  CATCATTGCATTTGTCTTGGCATTCTCCGTGGGAGCCAATGATGTAGCAAATTCGTTCGG   600
     ----+----+----+----+----+----+----+----+----+----+----+----+
 601  TACAGCTGTAGGCTCAGGTGTAGTGACCCTGAAGCAAGCCTGCATCTTAGCTAGCATCTT   660
 661  CGAAACTGTGGGCTCCGCCTTGCTGGGGGCCAAAGTGAGCGAAACCATCCGGAACGGCTT   720
 721  GATAGATGTGGAGCTGTACAACGAAACTCAAGATCTGCTCATGGCTGGCTCCGTCAGTGC   780
 781  TATGTTTGGTTCTGCTGTGTGGCAGCTCGTGGCTTCGTTTTTGAAGCTTCCGATTTCTGG   840
 841  GACCCATTGTATTGTCGGTGCAACCATTGGTTTCTCCCTTGTGGCAAATGGGCAGAAGGG   900
     ----+----+----+----+----+----+----+----+----+----+----+----+
 901  TGTCAAGTGGTCTGAACTGATAAAAATTGTGATGTCGTGGTTCGTCTCTCCGCTGCTTTC   960
 961  TGGTATTATGTCTGGAATTTTATTCTTCCTTGTTCGTGCGTTCATCCTCCGTAAGGCAGA  1020
1021  TCCGGTTCCTAATGGCTTACGAGCTTTACCAATTTTTTATGCCTGCACAATCGGAATCAA  1080
1081  CCTCTTTTCCATTATGTATACTGGAGCACCGTTGCTGGGCTTTGACAAACTTCCTCTGTG  1140
1141  GGTACCATCCTCATCTCGGTGGGATGTGCAGTTTTCTGTGCCCTTATCGTCTGGTTCTT   1200
     ----+----+----+----+----+----+----+----+----+----+----+----+
1201  TGTATGTCCCAGGATGAAGAGAAAAATTGAACGAGAAGTAAAGTCTAGTCCGTCTGAAAG  1260
1261  TCCCTTAATGGAAAAGAAGAGCAACTTAAAAGAAGACCATGAAGAAACAAAGATGGCTCC  1320
1321  TGGAGACGTTGAGCATAGGAATCCTGTGTCTGAGGTAGTGTGTGCCACTGGGCCACTCCG  1380
1381  GGCTGTGGTGGAGGAGAGGACGGTGTCATTCAAACTTGGTGACCTGGAGGAGGCTCCCGA  1440
1441  GCGAGAGCGGCTTCCCATGGACCTGAAGGAGGAGACCAGCATAGACAGCACCATCAATGG  1500
     ----+----+----+----+----+----+----+----+----+----+----+----+
1501  TGCAGTGCAGTTGCCTAATGGGAACCTTGTTCAGTTCAGTCAAACTGTCAGCAACCAGAT  1560
1561  CAACTCCAGTGGCCACTATCAGTATCACACCGTGCACAAGGATTCTGGCTTGTACAAGGA  1620
1621  GCTGCTCCATAAGTTACATCTGGCCAAGGTGGGAGACTGCATGGGAGATTCTGGGGACAA  1680
1681  GCCCTTGAGACGCAACAACAGCTACACTTCCTACACTATGGCAATATGTGGCATGCCCCT  1740
1741  GGATTCATTCCGTGCCAAAGAAGGTGAACAAAAGGGAGATGAAATGGAGACGCTGACATG  1800
     ----+----+----+----+----+----+----+----+----+----+----+----+
1801  GCCTAATGCAGATACCAAGAAGCGGATTCGAATGGACAGTTACACCAGTTACTGCAATGC  1860
1861  CGTGTCTGACCTTCACTCCGAGTCTGAGATGGACATGAGTGTGAAGGCTGAGATGGGCCT  1920
1921  GGGTGACAGAAAAGGAAGCAGTGGCTCTCTTGAAGAATGGTATGACCAGGATAAGCCTGA  1980
1981  AGTGTCCCTTCTCTTCCAGTTCCTGCAGATCCTTACAGCCTGCTTTGGGTCATTTGCCCA  2040
2041  TGGTGGCAATGACGTCAGCAATGCCATCGGCCCTCTGGTTGCTTTGTATCTTGTTTATAA  2100
```

FIG. 9A

```
2101  ACAAGAAGCCTCTACAAAAGCGGCAACACCCATATGGCTTCTGCTTTATGGTGGTGTTGG  2160
2161  CATTTGCATGGGCCTGTGGGTTTGGGGAAGAAGAGTTATCCAGACCATGGGGAAGGACCT  2220
2221  GACCCCAATCACACCCTCCAGTGGTTTCAGTATTGAACTGGCGTCTGCCTTAACTGTGGT  2280
2281  CATCGCATCAAACATTGGCCTTCCCATCAGCACAACACATTGCAAAGTGGGCTCTGTTGT  2340
2341  GTCTGTTGGCTGGCTCCGATCAAAGAAGGCTGTTGACTGGCGACTGTTTCGAAACATTTT  2400

2401  TATGGCCTGGTTTGTCACGGTCCCCATCTCTGGGGTTATCAGTGCCGCTATCATGGCAGT  2460
2461  ATTCAAGTACATCATCCTGCCAGTGTGACGCTGGGGTTGAAAGCTGTGTCAGTGTCTGGG  2520
2521  ACCATTGTACACATTCCTGTTCCTAGGAGAACGCTCACAGTGTTGCTGAAGACAGGCAAG  2580
2581  GGTCTTAAAGGAGCCGTGGGAAGGAAGTGTAATTTACACTATAATTGCTTTTGTGCTAAA  2640
2641  TATGACTTATCTCAAAATTAGCTATGTAAAATAGCCAGGTTTCCATTGATTCATTCCAAG  2700

2701  GTCCCTTTTCTCCTGGGCTATGAATTCCTGTACATATTTCTCTACTTTTGTATCAGGCCT  2760
2761  CAATTCCAGTATGTTTTAATGTTGTCTGTGAGATAACTTAGGTGGGTTCTTTTTAAACAG  2820
2821  CCAGCAGAGCCATTTGATGGCATGTACTGCTTTGTCGGCCTCACCAGCTTCTTCCCCAAC  2880
2881  ATGCACAGGGATTTAACAACATGTAACTGAAGCTTCCCTCCCTCATAGTCTCTCATAGAA  2940
2941  ATAGTCACGGCACTCTGCTCCCTGTCACTAGTGGCAGGTTCTGTTGATGTGTGACAACTT  3000

3001  CTTAGAGGGCCGAGAATCTTTGGCACAGTGGAAATATAAGTTTGTAGTAACCTCTTTGCA  3060
3061  AACAGTTCACGGACATGTTGCTAAGAAGCAGGGAGACAAAGCCCCTGGCGGTTGTGGTTA  3120
3121  TTCTTCTGAGATTTCTGGCAGTGTGGGATGGGTGAATGAAGTGGAATGTGAACTTTGGGC  3180
3181  AAATTCAATGGGACAGCCTTCCATGTTCATCTGTCTACCTCTTAACTGAATAAAAAGCCT  3240
3241  ACAGTTTTAAAAAAAAAAAA                                          3268
```

FIG.9B

```
                                    ▼10              ▼20              ▼30              ▼40              ▼50
mouse Glvr-1 prot     VATITSTLAAVTASAPPKYDNLWMLILGFIIAFVLAFSVGANDVANSFGT
                     :AT:.::  :A.TA::   P  D LWMLILGFIIAFVLAFSVGANDVANSFGT
hum GLVR1 prot        MATLITSTTAATAASGPLVDYLWMLILGFIIAFVLAFSVGANDVANSFGT
                                    ▲10              ▲20              ▲30              ▲40              ▲50

▼60              ▼70              ▼80              ▼90              ▼100
mouse Glvr-1 prot     AVGSGVVTLKQACILASIFETVGSALLGAKVSETIRNGLIDVELYNETQD
                     AVGSGVVTLKQACILASIFETVGS.LLGAKVSETIR:GLIDVE:YN.TQ:
hum GLVR1 prot        AVGSGVVTLKQACILASIFETVGSVLLGAKVSETIRKGLIDVEMYNSTQG
                                    ▲60              ▲70              ▲80              ▲90              ▲100

▼110             ▼120             ▼130             ▼140             ▼150
mouse Glvr-1 prot     LLMAGSVSAMFGSAVWQLVASFLKLPISGTHCIVGATIGFSLVANGQKGV
                     LLMAGSVSAMFGSAVWQLVASFLKLPISGTHCIVGATIGFSLVA:GQ.GV
hum GLVR1 prot        LLMAGSVSAMFGSAVWQLVASFLKLPISGTHCIVGATIGFSLVAKGQEGV
                                    ▲110             ▲120             ▲130             ▲140             ▲150

▼160             ▼170             ▼180             ▼190             ▼200
mouse Glvr-1 prot     KWSELIKIVMSWFVSPLLSGIMSGILFFLVRAFILRKADPVPNGLRALPI
                     KWSELIKIVMSWFVSPLLSGIMSGILFFLVRAFIL:KADPVPNGLRALP:
hum GLVR1 prot        KWSELIKIVMSWFVSPLLSGIMSGILFFLVRAFILHKADPVPNGLRALPV
                                    ▲160             ▲170             ▲180             ▲190             ▲200

▼210             ▼220             ▼230             ▼240             ▼250
mouse Glvr-1 prot     FYACTIGINLFSIMYTGAPLLGFDKLPLWGTILISVGCAVFCALIVWFFV
                     FYACT:GINLFSIMYTGAPLLGFDKLPLWGTILISVGCAVFCALIVWFFV
hum GLVR1 prot        FYACTVGINLFSIMYTGAPLLGFDKLPLWGTILISVGCAVFCALIVWFFV
                                    ▲210             ▲220             ▲230             ▲240             ▲250

▼260             ▼270             ▼280             ▼290             ▼300
mouse Glvr-1 prot     CPRMKRKIEREVKSSPSESPLMEKKSNLKEDHEETKMAPGDVEHRNPVSE
                     CPRMKRKIERE:K.SPSESPLMEKK::LKEDHEETK:.  GD: E:::PVSE
hum GLVR1 prot        CPRMKRKIEREIKCSPSESPLMEKKNSLKEDHEETKLSVGDIENKHPVSE
                                    ▲260             ▲270             ▲280             ▲290             ▲300

▼310             ▼320             ▼330             ▼340             ▼350
mouse Glvr-1 prot     VVCATGPLRAVVEERTVSFKLGDLEEAPERERLP-MDLKEETSIDSTING
                     V  AT PL: AVVEERTVSFKLGDLEEAPERERLP :DLKEETSIDST:NG
hum GLVR1 prot        VGPATVPLQAVVEERTVSFKLGDLEEAPERERLPSVDLKEETSIDSTVNG
                                    ▲310             ▲320             ▲330             ▲340             ▲350
```

```
                      ▼360            ▼370            ▼380            ▼390            ▼400
mouse Glvr-1 prot     AVQLPNGNLVQFSQTVSNQINSSGHYQYHTVHKDSGLYKELLHKLHLAKV
hum GLVR1 prot        AVQLPNGNLVQFSQ:VSNQINSSGH QYHTVHKDSGLYKELLHKLHLAKV
                      ▲360            ▲370            ▲380            ▲390            ▲400

▼410            ▼420            ▼430            ▼440            ▼450
mouse Glvr-1 prot     GDCMGDSGDKPLRRNNSYTSYTMAICGMPLDSFRAKEGEQKGDEMETLTW
hum GLVR1 prot        GDCMGDSGDKPLRRNNSYTSYTMAICGMPLDSFRAKEGEQKG:EME.LTW
                      ▲410            ▲420            ▲430            ▲440            ▲450

▼460            ▼470            ▼480            ▼490            ▼500
mouse Glvr-1 prot     PNADTKKRIRMDSYTSYCNAVSDLHSESEMDMSVKAEMGLGDRKGSSGSL
hum GLVR1 prot        PNADSKKRIRMDSYTSYCNAVSDLHSASEIDMSVKAAMGLGDRKGSNGSL
                      ▲460            ▲470            ▲480            ▲490            ▲500

▼510            ▼520            ▼530            ▼540            ▼550
mouse Glvr-1 prot     EEWYDQDKPEVSLLFQFLQILTACFGSFAHGGNDVSNAIGPLVALYLVY-
hum GLVR1 prot        EEWYDQDKPEVSLLFQFLQILTACFGSFAHGGNDVSNAIGPLVALYLVY
                      ▲510            ▲520            ▲530            ▲540            ▲550

▼560            ▼570            ▼580            ▼590            ▼600
mouse Glvr-1 prot     KQEASTKAATPIWLLLYGGVICMGLWVWGRRVIQTMGKDLTPITPSSGF
hum GLVR1 prot        TGDVSSKVATPIWLLLYGGVICVGLWVWGRRVIQTMGKDLTPITPSSGF
                      ▲560            ▲570            ▲580            ▲590            ▲600

▼610            ▼620            ▼630            ▼640            ▼650
mouse Glvr-1 prot     SIELASALTVVIASNIGLPISTTHCKVGSVVSVGWLRSKKAVDWRLFRNI
hum GLVR1 prot        SIELASALTVVIASNIGLPISTTHCKVGSVVSVGWLRSKKAVDWRLFRNI
                      ▲610            ▲620            ▲630            ▲640            ▲650

▼660            ▼670            ▼680
mouse Glvr-1 prot     FMAWFVTVPISGVISAAIMAVFKYIILPV
hum GLVR1 prot        FMAWFVTVPISGVISAAIMA:F:Y:IL.:
                      ▲660            ▲670
                                      FMAWFVTVPISGVISAAIMAIFRYVILRM
```

DNA ENCODING GIBBON APE LEUKEMIA VIRUS RECEPTOR

RELATED APPLICATIONS

This is a continuation-in-part of U.S. Ser. No. 398,351, filed Aug. 24, 1989, now abandoned, the contents of which are incorporated by reference herein in their entirety.

BACKGROUND OF THE INVENTION

The present invention relates to the receptor protein for gibbon ape leukemia virus, a retrovirus and to animal genes and their proteins which interact with gibbon ape leukemia virus (GALV). These GALV receptor proteins are required for entry of the virus into cells, and are therefore defined as cellular receptors for GALV.

Retroviruses can be placed into specified groups depending on the pathway used by the viruses to enter cells. It is thought that members of one given group utilize specific cellular receptors for entry into cells and that there is little, if any, cross-utilization of receptors by members of different groups. In general, these receptors have remained virtually unexplored. Of the approximately eight human receptors specific for the retroviruses known to infect human cells, only one has been cloned (CD4 for HIV; Maddon et al., 1986; McDougal et al., 1986). This invention therefore relates to one of the currently known receptors required for infection of animals, specifically human cells, by a retrovirus. Although the presence of a specific receptor protein for GALV (and for other retroviruses utilizing other receptor pathways) has been speculated, no GALV-specific receptor has heretofore been cloned or characterized.

While mention has been made of GALV, it is understood that simian sarcoma-associated virus and other viruses as stated above, utilize the same receptor (Weiss et al., 1984).

The novel genes and proteins of the present invention are useful in experimental manipulation of the GALV host, in analysis of virus/receptor interactions, and in elucidation and exploitation of the normal role of the receptor, which may include functions in substrate/ion transport and/or in immune activity.

BRIEF DESCRIPTION OF THE DRAWINGS

FIG. 6. DNA sequence of the human cDNA for the GALV receptor (Seq. I.D. #1). The long open reading frame extends from positions 371 to 2407, inclusively.

FIG. 7. Amino acid sequence (Seq. I.D. #2) of the human GALV receptor protein, as derived from the long open reading frame in FIG. 6.

FIG. 9. Nucleotide sequence of Glvr-1 (Seq. I.D. #3). The sequence is a composite of pMGR1 (bases 1–2777) and pMGR2 (bases 1113–3260). The ATG and TAG codons defining the long open reading frame and the presumptive polyadenylation signal are underlined. EcoRI linkers added during cloning are not indicated.

FIG. 10. Comparison of the human and murine GALV receptor protein sequences (Seq. I.D. #2 and 3, respectively) using the method of Needleman and Wunsch, 1970. In the Sequence Listings, Xaa indicates the position of the stop codon.

SUMMARY OF THE INVENTION

Figure 4:
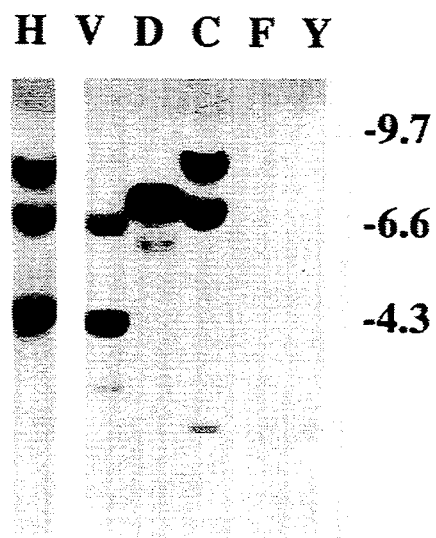
FIG. 4. Southern analysis of EcoRI-digested human (H), African green monkey vero cell (V), dog (D), cat (C), frog (F) and yeast (Y) DNAs using the 5' EcoRI insert fragment of lambda HGR6 (subcloned in pUC118) as probe.

The present invention relates to the GALV protein receptor and its homologs expressed in a wide variety of animal tissues. The primary amino acid sequence of the human receptor is illustrated in FIG. 7. However, as would be expected from the wide host range of GALV (Weiss et al., 1984) and from Southern analysis of species other than human (FIG. 4), closely-related homologs exist in species such as dog, cat, mouse and monkey, and others. The amino acid sequence of the corresponding mouse protein is provided in FIG. 10. These observations support the universal existence of discrete genes truly homologous to the human GALV receptor. Thus, the present invention relates not only to the specific proteins identified in FIGS. 7 and 10, but also to proteins having substantially the same sequence and/or substantially the same capacity to allow viral infection as the protein illustrated in FIGS. 7 and 10. Further, the invention relates to the purified DNA sequence (See, e.g., FIGS. 6 and 9) coding for the human (GALV) receptor (also referred to as GLVR1 [human] or Glvr-1 [mouse]) and to DNAs having substantially the same DNA sequence encoding substantially the same amino acid sequence as the DNA in FIGS. 6 and 9. It is appreciated by those of ordinary skill in the art that other such proteins from other species, as well as other alternatives to the protein illustrated in FIGS. 7 and 10, are isolated by the process of the present invention. Various expression systems may be used to produce varieties to those proteins but such varieties still result in a protein with similar biological activities to the present protein. It is also recognized by those skilled in the art that modifications to the DNA sequence presented in FIGS. 6 and 9 results in GALV receptor proteins. The resultant DNA sequences and resulting proteins having substantially the same role in allowing viral entry are included within the scope of the invention. The biological function of the receptor is measured by infection studies of cells normally not infectable and transfected with constructs designed to express the protein (as demonstrated in Table 1). Further, antibody binding studies characterize and identify amino acid sequence and structure. Virus infection studies functionally identify a protein's role in allowing viral entry.

The GALV receptor proteins of the present invention are produced through expression vectors comprising a DNA sequence encoding a GALV receptor protein (including human, mouse or DNA sequences of the homologs of other species) or mutants (with or without the ability to confer susceptibility to infection on normally uninfectable cells) wherein one or more amino acids have been inserted, deleted, or substituted in or from the amino acid sequence of the human or mouse GALV receptor protein or of their homologs from other species. The invention also relates to biologically active fragments of the whole receptor protein, i.e., those portions of the molecule which confer binding ability, and/or antigenicity, and/or substrate/ion transport ability.

Additionally, the present invention includes a method for identifying GALV receptor homologs of all animal species wherein a DNA probe selected from the DNA in FIG. 6 or 9 or with substantially the same DNA sequence as that identified in FIG. 6 or 9 is used to isolate the appropriate DNA from the other species.

Further, as can be determined by those skilled in the art, the manipulation of the GALV receptor allows for regulation of viral entry into cells. This may allow the prevention of certain viral infections and the ability to control this mechanism for retroviruses utilizing the GALV receptor protein for cellular entry. The protein per se can be used to screen compounds which bind to the receptor. Such compounds can be used therapeutically to bind the receptor, thereby preventing viral entry at these sites. A therapeutically effective amount of a GALV-receptor binding agent is used to manipulate cellular infectivity for retroviruses. Additionally, the solubilized receptor, or biologically active fragment thereof, can be administered to a host so as to bind and inactivate virus.

For purposes of the present invention, the plasmids, DNA sequences, and microorganisms deposited in connection with the present invention, except where specified to the contrary, are deposited in American Cyanamid Company's culture collection maintained in Pearl River, N.Y. and are deposited with American Type Culture Collection in Rockville, Md. 20952, U.S.A.

Although the use of genetic engineering techniques lend themselves to effective methods to produce the GALV receptor proteins of the present invention, it is equally to be noted that the present proteins encompass other methods of production, such as chemical synthesis or purification from animal tissues. Isolation of the protein can be achieved by any of the protein purification methods known in the art.

It is an object of the present invention, therefore to provide the novel receptor protein of the GALV receptor. Also, the GALV receptor protein of other animal species, besides the human GALV receptor protein, is encompassed by the present invention. Another object of the invention is to provide an isolated DNA sequence coding for the GALV receptor. These and other objects of the invention will become apparent by the more detailed description of the invention provided hereinbelow.

DETAILED DESCRIPTION OF THE INVENTION

The present invention relates to the GALV receptor protein. The species analyzed in greatest detail is the human, but data relating to the mouse sequences are also provided, and it is recognized that similar proteins exist in other animal species. Therefore, the invention includes those homologous proteins from other species. The present invention discloses the structure of cDNA for the GALV receptor from human HL60 cells and mouse thymus cells. Further, the functionality of the isolated cDNA in allowing viral entry is provided in the following examples but is not limitative thereof.

The studies reported below allow a comparison of human GLVR1 to its mouse homologue, Glvr-1, and provide a general characterization of Glvr-1 RNA expression in murine tissues. Comparison of the presumed proteins encoded in the human and mouse cDNAs reveals a high degree of homology, the long open reading frames being almost identical in length and coterminal. The homology includes three potential N-linked glycosylation sites at positions 100, 374 and 418 (that at position 497 in the human is not present in the murine cDNA) and 12 of the 13 cysteine residues present in each protein. Two of these cysteines are found in what appears to be a repeated region within the protein which is fully conserved between the two cDNAs. This repeat spans the sequences LPISGTHCIVG (residues 129–139 and 125–135 in mouse and human cDNA, respectively) and LPISTTHCKVG (residues 620–630 and 618–628 in mouse and human cDNA, respectively).

The positions at which the two proteins differ involve less than 10% of residues and many of these differences are conservative, having little or no effect on those regions of the protein which are highly hydrophobic and which are likely to represent transmembrane domains (O'Hara et al., 1990). The differences between the two proteins are not randomly distributed, being largely clustered in four groups. In order to define regions of the protein that are critical for infection, a series of clones is constructed by exchanging equivalent portions of human and murine cDNAs. These and several clones with deletions in GLVR1 are tested for their ability to confer susceptibility to infection. The results indicate that the terminal one-third of the protein is critical in controlling infectivity. The murine sequence differs from the human at three portions in this region, involving residues 553–560, 576 and 673–681. On the assumption that, of these three differences, residues 553–560 are the primary determinants of permissivity because they are hydrophilic and therefore might be available for binding by virus, the murine cDNA is therefore altered by in vitro mutagenesis to encode the corresponding human residues in this region only. This construct is found to readily confer susceptibility to infection, and therefore identify residues 550–558 of GLVR1 as critical for infection by GALV.

In the region 5' to the long open reading frame, several ATG codons are present in both cDNAs. Those in the human cDNA have the potential to initiate translation of only short peptides (O'Hara et al., 1990) and, except for one, do not conform to the consensus sequence for initiation of translation. In addition, these ATG codons are dispensible for confering the phenotype of sensitivity to infection, as we have shown here. The upstream ATG codons in the mouse cDNA also have the potential to initiate translation of only short peptides and only one (which is also conserved in the human) conforms well to the expected sequence for translation initiation. It is possible that these upstream open reading frames direct the translation of proteins with some as yet unknown function or may represent sequences involved in control of the expression of the GALV receptor protein. The present invention, therefore also encompasses these putative peptides and DNA sequences encoding them; the peptides are useful in production of antibodies, which in turn may be used in the study of the pattern of expression of the peptides in the cell.

Sequences conforming to the consensus sequence for polyadenylation are found at approximately the same positions in both cDNAs. Because the sequence in the murine cDNA is followed at 15 bases by a short polyA tract, these appear to be functional polyadenylation signals.

Glvr-1 RNA is detected at some level in almost all tissues. On the assumption that protein levels will generally reflect RNA levels, this suggests that the function of the gene is not peculiar to a specific cell type. This finding is in agreement with the sensitivity to infection in vitro of cells derived from a wide range of tissues (Weiss et al., 1984). Despite the widespread distribution of the RNA, the levels vary widely among different tissues. The level is by far highest in most compartments of the brain. Because internal capsule and brainstem are largely white matter and contain a level of RNA similar to those found in several other tissues (e.g., cortex) which are rich in grey matter, it appears that Glvr-1 expression is not favored in either white or grey matter. RNA levels are also found to be high in the thymus and in the spleen of an animal undergoing a graft-versus-host (GVH) reaction, where 60% of the spleen cells are constituted by activated graft cells. It may therefore be that T cells in vivo express high levels of Glvr-1. These findings of high levels of RNA in brain, thymus, and GVH spleen demonstrate a substantial degree of tissue-specificity in the expression of Glvr-1 and suggest that the protein may be particularly important in neurophysiology and in T cell function.

The locus is expressed at each stage of rat development in the tissues examined. A variation is found in whole embryos in early stages of embryogenesis, there being a notable increase in RNA at the ten-day stage as compared to the eight-day stage. Thereafter the RNA levels in heads and brains declined slightly until after birth, where it is found that adult brain expresses more RNA than is present in fetal or neonatal brain. These results suggest that the level of Glvr-1 expression may have developmental consequences.

It has recently been shown that Glvr-1 is tightly linked to the genes for interleukin-1 (Il-1) and the prion protein (Prn-P) on mouse chromosome 2 and is likely to be proximal to Prn-P (Kaelbling et al., 1991). It is possible that Glvr-1 is related or even identical to other loci mapped to this area. This applies in particular to the minor histocompatibility antigens H-3 and H-42 (Ishikawa et al., 1986; Kurtz et al., 1985). These antigens are likely to be cell surface markers, as is Glvr-1, and are apparently widely-expressed, which is also the case, as has been shown here. The relationship between Glvr-1 and markers in its immediate vicinity, including the minor histocompatibility antigens and several genes involved in development, remains to be determined.

Although the normal physiological role of the GALV receptor gene has not previously been clear, the gene now appears to be homologous with Pho-4, a phosphate permease of *Neurospora Crassa* (Mann et al., Gene 83:281–289, 1989), incorporated herein by reference. The homology is sufficient to allow the presumption that the GALV protein also acts as a permease. As such, the protein, and heterologous cells expressing the protein, can be readily used to study the process of ion or substrate transport, and can serve as the basis of a screen for pharmaceutical products to control ion/substrate transport.

EXAMPLE 1

Isolation of GALV Receptor

Portions of the human receptor gene (GLVR-1) for gibbon ape leukemia virus (GALV) are isolated in the following manner. Firstly, DNA from human cells (which are easily infected with GALV and therefore express that viral receptor) are introduced into mouse NIH3T3 cells (which cannot be infected with the virus) in one of a variety of ways, the procedure of $CaPO_4$ precipitation being described below. High molecular weight human DNA is mixed with pSV2gpt in aqueous solution containing $CaCl_2$ and the mixture is added to a second solution containing phosphate and HEPES buffer at pH 7.1. The DNAs precipitate together in aggregates with $CaPO_4$ and this aggregate is applied to cells in culture (mouse NIH3T3 cells). A portion of the cells takes up aggregates of the DNA mixture and incorporates and expresses the transfected DNA.

In order to study only those cells which have been transfected, selection is imposed for the presence of pSV2gpt. To do this, cells are grown in medium containing mycophenolic acid and xanthine. The mycophenolic acid imposes a metabolic block on the cells which can be overcome by the expression of guanosine phosphoribosyltransferase (encoded by pSV2gpt) through its utilization of xanthine (Mulligan and Berg, 1981). After about two weeks in this medium, only transfected cells remain. A given cell in this culture now expresses approximately 0.1% of the human donor DNA. A portion of these (approximately 1/1000) are expected to express the human receptor for GALV. Such cells are isolated by infection with an antibiotic-resistant virus which requires interaction with the GALV receptor to enter cells. This virus is made by rescuing pGV16, a G418-resistant, replication-defective virus (Noda et al., 1986) from cells, using GALV, such that the pGV16 pseudotyped by GALV (i.e., the pGV16 RNA genome is contained in a GALV particle). The mixture [termed pGV16(GALV)] can now only infect cells using the pathway regularly used by GALV. This mixture is applied to the transfected mouse cells and these are treated two days later with G418 antibiotic. Only cells infected with pGV16 survive. These are termed primary transfectants and should contain approximately 0.1% of the human genome in each independent isolate.

EXAMPLE 2

Transfection

The transfected material found in the primary transfectants will contain a large amount of human repetitive sequences and should also include the human GALV receptor gene. However, because the pressure for the maintenance of the gene is lost after infection with virus and selection for pGV16, many transfectants can be expected to have segregated the gene, as is normal for any such experiment. For this reason, a primary transfectant is sought which has been infected with pGV16 but not with the replication competent GALV. The continued presence of the receptor, and therefore of the receptor gene, can be demonstrated in such a cell because it is not immune to superinfection as are cells which have been infected with GALV. These constitute the majority of isolates because GALV is in excess over pGV16 in the pGV16(GALV) stocks. A transfectant infected only with pGV16 is chosen, in this case the cell termed GRT5, DNA is prepared from it, and the DNA used in a second round of transfection to obtain secondary transfectants. The process to obtain these is similar to that used to derive primary transfectants. That is, DNA from GRT5 is mixed with pSV2gpt, precipitated with CaPO4, and transfected into NIH3T3 cells. These are then grown in medium containing mycophenolic acid and xanthine and the surviving cells are infected with pGV16(GALV). G418 is then applied and surviving cells are grown up and examined to identify presumptive secondary transfectants for the receptor gene. Since proviral pGV16 is present in the primary donor DNA, some of the secondary transfectants will have become G418-resistant from transfection of the proviral DNA. The bona fide receptor transfectants can, however, be distinguished from these because the majority of the secondary transfectants are therefore screened for GALV production and DNA is prepared from any found. This DNA is analyzed in Southern analysis to determine if any of the producers contain human repetitive sequences. Because the processes of primary and secondary transfection successively reduce the amount of human repetitive DNA to be found in a transfectant, it is expected that any repetitive human DNA found in a secondary transfectant is specifically associated with the receptor gene.

EXAMPLE 3

Isolation of cDNA and cDNA Probes

Figure 1:
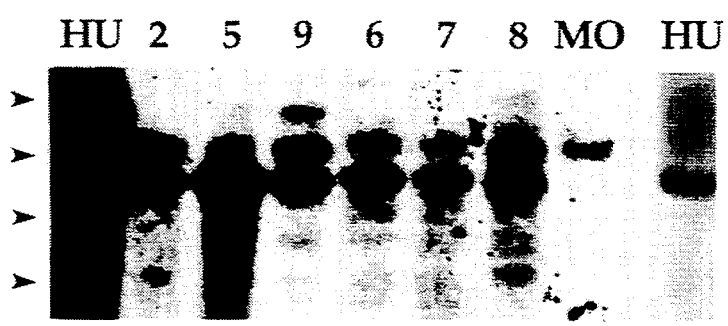
FIG. 1. Southern analysis of human (HU) transfectant (GRT), and mouse (MO) BamHI-digested DNAs. The left panel shows a blot hybridized with the entire (repeat-containing) 3.5 kb EcoRI insert of pR7h. The right lane is hybridized with the 2.2 kb EcoRI-HindIII subfragment.

A genomic library is constructed from any such secondary transfectants found in Example 2 (in this case GRT9, the secondary transfectant, and lambda gt10 and EcoRI as the vector and cloning enzyme, respectively) and screened for the presence of clones containing human repetitive DNA using human DNA made radioactive in nick translation as probe. One in 500,000 clones is found to hybridize with the probe. This clone (lambda R7h) is plaque-purified to homogeneity and its 3.5 kb EcoRI insert is cloned in pGEM2 and pUC118. This 3.5 kb EcoRI fragment is found to consist of 2.2 and 1.3 kb EcoRI-HindIII fragments. Use of the entire 3.5 kb fragment as probe in Southern analysis demonstrates that the cloned DNA contains human repetitive sequences, as expected, and that it hybridizes to a 6.6 kb EcoRI fragment in most of the transfectants but not appreciably to mouse DNA (FIG. 1, longer exposure times reveal the presence of a hybridizing band in mouse DNA representing the murine homolog, as expected). The presence of this latter transfected sequence in independent transfectants demonstrates that the sequences in lambda R7h are part of or are in close proximity to the receptor gene. Use of the 2.2 kb fragment as probe gives the same result except that in human DNA only a single fragment of 6.6 kb is detected (FIG. 1). This indicates that only single copy sequences are contained in this fragment.

Figure 2:
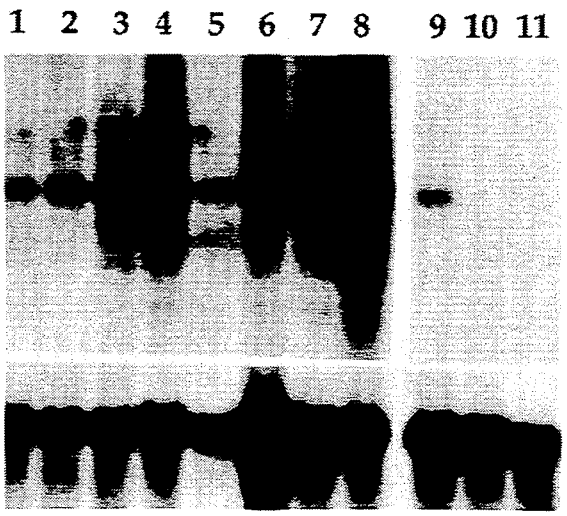
FIG. 2. Northern analysis of human, transfectant, and mouse RNAs. Probes used are the 2.2 kb EcoRI-HindIII subfragment of pR7h (upper panel) and an actin probe (lower panel; O'Hara et al., 1987). Lanes 1–4, total cellular oligo-dT purified RNA of the human cell line TU1.1.1 (O'Hara et al., 1987) Lane 1, confluent cells. 2, log-phase. 3, confluent GALV-infected. 4, confluent Mo-MuSV(GALV)-infected. Lanes 5–8, total cellular oligo-dT purified RNA of the human cell line NT2.1.1 (O'Hara et al., 1987). Lane 5, confluent. 6, log-phase. 7, confluent GALV-infected. 8, confluent Mo-MuSV(GALV)-infected. 9–11, cytoplasmic oligo-dT purified RNAs of primary transfectant GRT5, secondary transfectant GRT9, and NIH3T3 cells. resp.
Figure 5:
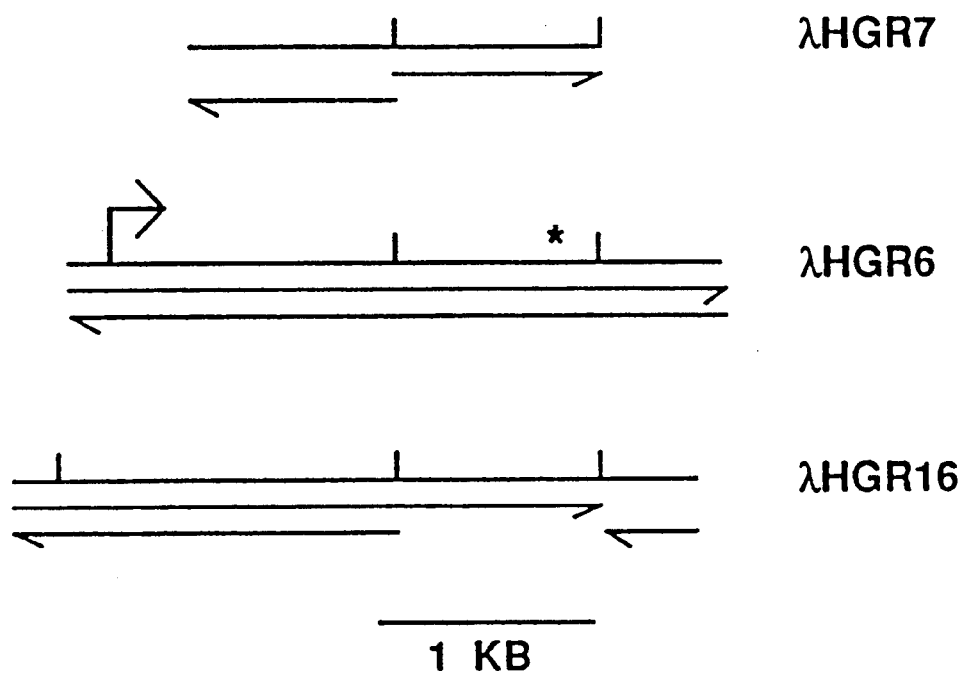
FIG. 5. Human cDNAs isolated and the strands sequenced. Notches represent EcoRI sites. EcoRI linkers are present at each end of each clone where no notch is indicated. The long open reading frame is indicated for lambda HGR6 by the arrow (translation start) and asterisk (termination codon).

When this fragment is used as probe in northern analysis, a single mRNA of approximately 4 kb is detected in human cells and in GRT5, the transfectant with the highest copy number for the transfected DNA; no strongly hybridizing RNA is found in mouse cells (FIG. 2). This indicates that the cloned sequences are expressed in RNA and are therefore suitable for screening cDNA libraries. Accordingly, a cDNA library from human HL60 cells (obtained from Clontech, #HL1020b) is screened with the fragment and 1/10,000 plaques are found to hybridize. Three of these (lambda isolates HGR6, HGR7, and HGR16, FIG. 5) are purified and the EcoRI fragments contained are subcloned in pUC118 and sequenced using the dideoxy termination method.

Analysis of the sequences reveals several features.
1. The sequences of the clones are virtually identical.
2. Lambda HGR6 and lambda HGR16 contain a single large open reading frame of 679 amino acids each, the presumptive amino acid sequences of which are identical.
3. Lambda HGR7 appears to be a truncated cDNA in that it contains a large open reading frame with an identical presumptive amino acid sequence for the 3'two-thirds of the presumptive protein encoded by the above isolates starting at amino acid 180 in FIG. 7.
4. The presumptive protein encoded by these isolates (FIG. 7) has the characteristics of an integral membrane protein. That is, analysis by the program of Kyte and Doolittle (1982) indicates several regions as possible membrane-spanning domains (these are approximately residues 15–39, 159–182, 228–251 and 651–674). Other regions are also hydrophobic, though to a lesser degree, and may also represent membrane-spanning domains (for example, regions 56–79, 118–141 and 555–578). The similarity of the presumed protein to integral membrane proteins is in keeping with its expected function as a retroviral receptor.

Figure 3A:
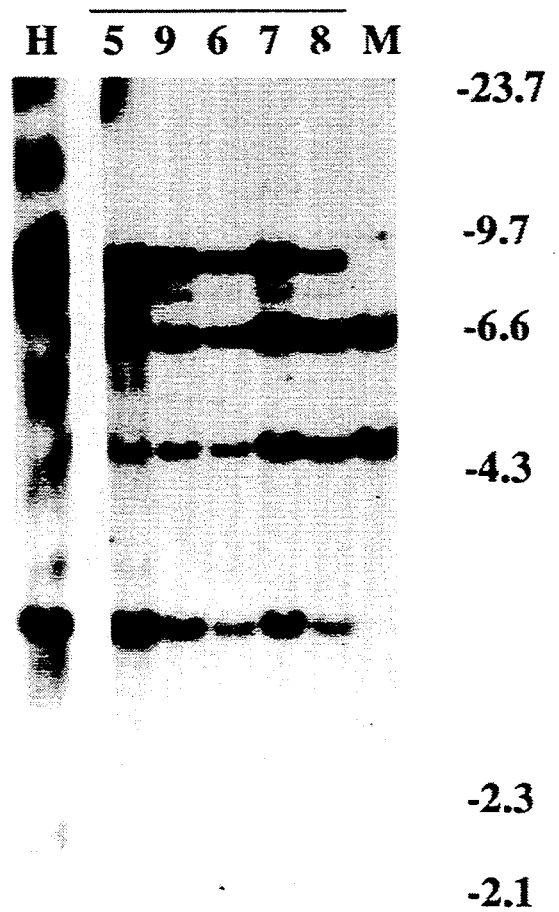
FIGS. 3A–3C. Southern and Northern analysis using cDNA probes. (A) Southern analysis of HindIII-digested human (H), transfectant (GRT), and mouse NIH3T3 (M) DNAs using the 5' EcoRI insert fragment of lambda HGR6 (subcloned in pUC118) as probe. (B) Southern analysis of EcoRI-digested DNAs using the middle EcoRI fragment of lambda HGR6 (subcloned in pUC118 as probe. (C) Northern analysis of oligo-dT-purified RNAs. Lane 1, NT2.1.1 RNA hybridized with a single-standard RNA probe derived from the 5' EcoRI fragment of lambda HGR6 and transcribed in the 3'-5' direction as indicated in FIG. 6. Lane 2 and 3 GRT-5 and NT2.1.1 RNAs hybridized with the three EcoRI inserts of lambda HGR6 (subcloned in pUC118) as probe.
Figure 3B:
Figure 3C:
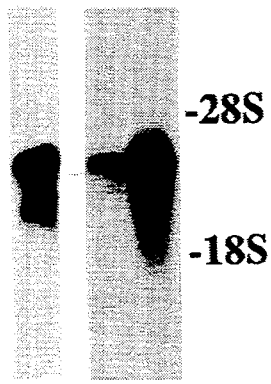

To further characterize the isolates, EcoRI fragments subcloned from lambda HGR6 are used in Southern analysis of human, transfectant and mouse DNAs. It is found that all fragments detected in human DNA are also found in transfectant DNAs but not in mouse DNA (FIGS. 3A, B). This further confirms that the isolates are derived from the receptor gene because such a great length of sequence would not be found in independent transfectants unless its presence had been selected for. FIG. 3C shows that the expected RNA is detected using cDNA probes.

EXAMPLE 4

Expression

Figure 8:
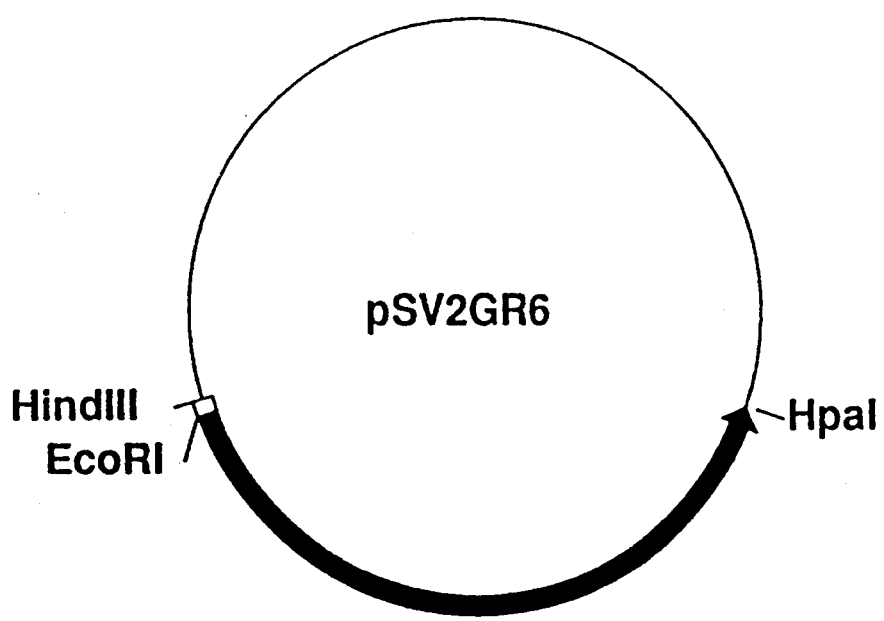
FIG. 8. Structure of pSV2GR6. The thin black line represents sequences derived from pSV2gpt. The small box represents sequences derived from the multiple cloning site of pUC118, and the arrowed box represents sequences derived from the insert of lambda HGR6. For this construction, lambda HGR6 is digested partially with EcoRI and the three contiguous EcoRI inserts are isolated as a single fragment. This is then cloned at the EcoRI site in pUC118 (to give pHGR6-1), so that the presumed 5' end of the insert is proximal to the HindIII site in pUC118. The portion of this plasmid between the HindIII and HpaI sites is cloned between the HindIII and HpaI sites of pSV2gpt to give pSV2GR6.

The ultimate proof that lambda HGR6 encodes the GALV receptor is derived by demonstrating its potential to confer susceptibility to GALV infection on mouse cells. pHGR6-1, containing the three EcoRI insert fragments of lambda HGR6 in the proper orientation, is digested with HindIII, which cuts in the multiple cloning site of the pUC118 vector at the 5' end of the insert, and with HpaI, which cuts in the 3' untranslated region of the insert. This fragment is used to replace the region of pSV2gpt between the HindIII and HpaI sites. The resulting plasmid, pSV2GR6 (FIG. 8), contains the entire open reading frame encoding the receptor with the SV40 early promoter upstream and an SV40 polyadenylation signal downstream. Mouse cells transfected with this plasmid are rendered susceptible to GALV infection, providing final confirmation that the clone does in fact encode the GALV receptor. Using the infectious center assay, up to 1% of the cells transfected with pSV2gpt and pSV2GR6 and selected for the presence of pSV2gpt are found to be infectable.

The plasmid pSV2GR6, containing the human GLVR-1, is deposited in the American Type Culture Collection as deposit number ATCC 68070 (Aug. 2, 1989).

TABLE 1

Expression of pSV2GR6 Renders Mouse NIH3T3 Cells Susceptible to Infection by GALV

| DNA Transfected | IC[a] | G418[R] No Virus | colonies[b] pGV16(GALV) |
|---|---|---|---|
| pSV2gpt | 0/10[5] | ND | 0/10[6] |
| pSV2gpt + pSV2GR6 | 739/10[5] | 0/10[7] | 252/6 × 10[6] |

Notes
[a]Number of cells producing virus/number tested. NIH3T3 cells (transfected and then grown in medium containing mycophenolic acid) were exposed to pGV16(GALV) and plated with PG4 cells in an infectious center assay.
[b]Colonies formed in medium containing G418/number tested. NIH3T3 cells (transfected and then grown in medium containing mycophenolic acid) were plated in the presence of G418 after exposure, where indicated, to pGV16(GALV)
ND Not Done

EXAMPLE 5

Cloning of Murine Glvr-1

A mouse thymus library (Stratagene 935303) in λ ZAP was screened with two EcoRI fragments containing bases 1-2659 of the human GLVR1 cDNA-containing clone pHGR6-1 (O'Hara et al., 1990). Hybridizing phage were plaque-purified and their inserts were excised in pBluescript SK— (Stratagene) by co-infection with helper phage, as described by the manufacturers. Sequencing was performed using single-stranded DNA templates and synthetic oligonucleotide primers (Vieira and Messing, 1987; Santer et al., 1977).

Seven cDNA clones are obtained after screening of 50,000 plaques from a mouse thymus library with a GLVR1-specific probe. One of these (pMGR1) contains an entire open reading frame similar to the open reading frame in the human cDNA and a substantial portion of upstream sequence. pMRG2 contains most of the open reading frame and, apparently, all of the 3' untranslated sequence, as it has a short poly A stretch 15 bases after a polyadenylation signal. FIG. 9 shows a composite of the sequences from pMGR1 and 2. It can be seen that Glvr-1 has the potential to encode a protein of 681 amino acid residues in its longest open reading frame (which is very similar in length to the presumed 679 residue human protein). An ATG codon closely resembling the consensus sequence for translation start (Kozak, 1986) initiates the open reading frame. Upstream of this codon, four other ATG codons are found (at positions 100, 132, 174 and 203). Those at positions 100 and 132 are not conserved in the human cDNA, do not closely fit the translation start sequence, and have the potential to initiate coding for peptides of only 25 and 31 residues, respectively. The ATG codon at position 174 is conserved in the human (position 106), fits the consensus sequence poorly in the human and only moderately well in the murine cDNA, and can direct synthesis of peptides of only 17 residues (almost identical in sequence) in each species. The ATG at position 203 in the murine is conserved relative to the human (position 135 in the human) and fits the translation start consensus sequence well in both species. Translation from these ATG codons would give similar peptides of 25 (human) and 26 (murine) residues. In the human sequence, at position 192 is an ATG codon encoding a six amino acid peptide with no corresponding murine peptide. The presence of polyadenylation signal sequences in the 3' regions of both human and mouse cDNAs, (followed in the mouse cDNA by a short polyA stretch) identifies the signal which is likely to be used in both species. Overall, the DNA sequence homology between the human and mouse cDNAs is approximately 90%.

FIG. 10 shows the presumed protein sequence of Glvr-1 and a comparison of the murine and human protein sequences. The two proteins differ at less than 10% of residues. The residues which differ are distributed throughout the protein but show a tendency to cluster in four areas. There is a region of considerable variation between the two proteins at the amino terminus. Residues 291–313 differ considerably from those in the human protein. In the carboxy-terminal third, two areas are substantially different: residues 553–561 and 673–681 in the murine cDNA compared to 550–558 and 671–679 in the human cDNA.

The plasmid pOJ19, containing the full-length mouse glvr-1 sequence, is deposited with the American Type Culture Collection as Accession No. 68517 (Jan. 24, 1991).

EXAMPLE 6

Definition of the Minimal Open Reading Frame Conferring Sensitivity to Viral Infection As mentioned, both human and mouse cDNAs contained ATG codons upstream of the codon initiating the long open reading frame. In order to assess their significance, it is necessary to test the effect on function of removing them. The only known function associated with the locus is the ability to confer sensitivity to infection by GALV and only the human cDNA will achieve this. Therefore, pOJ9, encoding the human cDNA but lacking ATG codons upstream of that initiating the long open reading frame, is constructed and tested for the ability to confer sensitivity to infection on mouse cells.

The construct is made in which the ATG codons normally present in the cDNA upstream of the ATG initiating the long open reading frame were removed. The sequence CATCTT (bases 318-323 in the human cDNA; O'Hara et al., 1990) is changed to the HindIII recognition sequence, AAGCTT, by in vitro mutagenesis. The HpaI site at position 2490 is changed to a BglII site by linker addition. The HindIII-BglII fragment is cloned into the eukaryotic expression vector, pcDNA1 (Invitrogen), between the HindIII and BamHI sites. This vector therefore carries the long open reading frame of GLVR1 cDNA under control of a cytomegalovirus promoter.

To test pOJ9, NIH3T3 cells, plated one day previously at $3 \times 10^5$/60 mm dish, are transfected with 1 μg pSV2neo or with pSV2neo and 3 μg pOJ9 or pSV2GR6 and carrier to 20 μg total DNA per dish, using CaPO$_4$ precipitation. pSV2neo confers resistance to the antibiotic G418 (Southern and Berg, 1982). pSV2GR6 contains the entire human GLVR1 cDNA, including the region with the three ATG codons upstream of the ATG initiating the long open frame, under control of the SV40 promoter (O'Hara et al., 1990). Three dishes are transfected with each precipitate. After two days, the cells are replated in medium containing G418 and colonies are allowed to form. Each of the nine dishes gives 80-200 colonies. Colonies derived from each dish are pooled and replated in each of two 60 mm dishes at $10^5$/dish with 4 μg/ml Polybrene (Sigma). After one day, one dish from each pool is exposed to 1 ml of GALV ($10^6$/ml). After a further two days, $10^4$ cells from each pool are replated with $3 \times 10^5$ PG4 S+L$^{-indicator}$ cells (Haapala et al., 1985). The small proportion of viruses used for the infection surviving to this stage are destroyed by trypsinization prior to replating with the indicator cells. Foci initiated by productively-infected NIH3T3 cells are counted after five days cocultivation with PG4 cells.

Table 2 shows that NIH3T3 cells, which are not normally susceptible to infection by GALV, become susceptible after transfection with pOJ9. The efficiency with which this is achieved is no less than, and in fact slightly better than, the results obtained with pSV2GR6. This plasmid contains most of the GLVR1 cDNA, including the three upstream ATG codons, and has been previously shown to confer sensitivity to infection by GALV (O'Hara et al., 1990). This result establishes that expression of the protein from the first ATG in pOJ9, without the potential for co-expression of the small upstream open reading frames, confers the phenotype of sensitivity to infection.

TABLE 2 pOJ9 Renders NIH3T3 Cells Sensitive to Infection by GALV

| Plasmid | Foci/$3 \times 10^4$ Cells | |
|---|---|---|
| | No GALV | GALV |
| pSV2neo | Not Done | 0 |
| pSV2neo + pSV2GR6 | 0 | 382 |
| pSV2neo + pOJ9 | 0 | 1000 |

NIH3T3 cells were transfected with the indicated plasmids and selected in G418. Pooled colonies were exposed to virus and tested for infection using indicator cells as described above.

EXAMPLE 7

Glvr-1 RNA Levels in Mouse Tissues

In order to study Glvr-1 RNA levels in mouse tissue, total RNA is prepared from quick-frozen and disrupted tissues as described (Glisin et al., 1974) and subjected to northern analysis. Hybridization is carried out in 50% formamide, $5 \times$ SSC, $5 \times$ Denhardt's, 0.1% SDS, and 200 μg/ml sonicated, denatured salmon sperm DNA, at 42° C. The probe used is the entire pMGR1 labeled by nick translation using $^{32}$p DCTP. Washing is to a final stringency of $0.1 \times$ SSC, 0.1% SDS, at 65° C. For most mouse tissues, C57 BL $6 \times$ DBA/2 F$_1$ hybrids are used. For spleen undergoing a graft-versus-host reaction, an F$_1$ hybrid is injected with $5 \times 10^6$ C57 BL6 spleen cells and the host spleen is removed for RNA preparation eight days after injection. Rat tissues are from Sprague-Dawley rats and are prepared at the developmental stages indicated in the figures.

Figure 11:
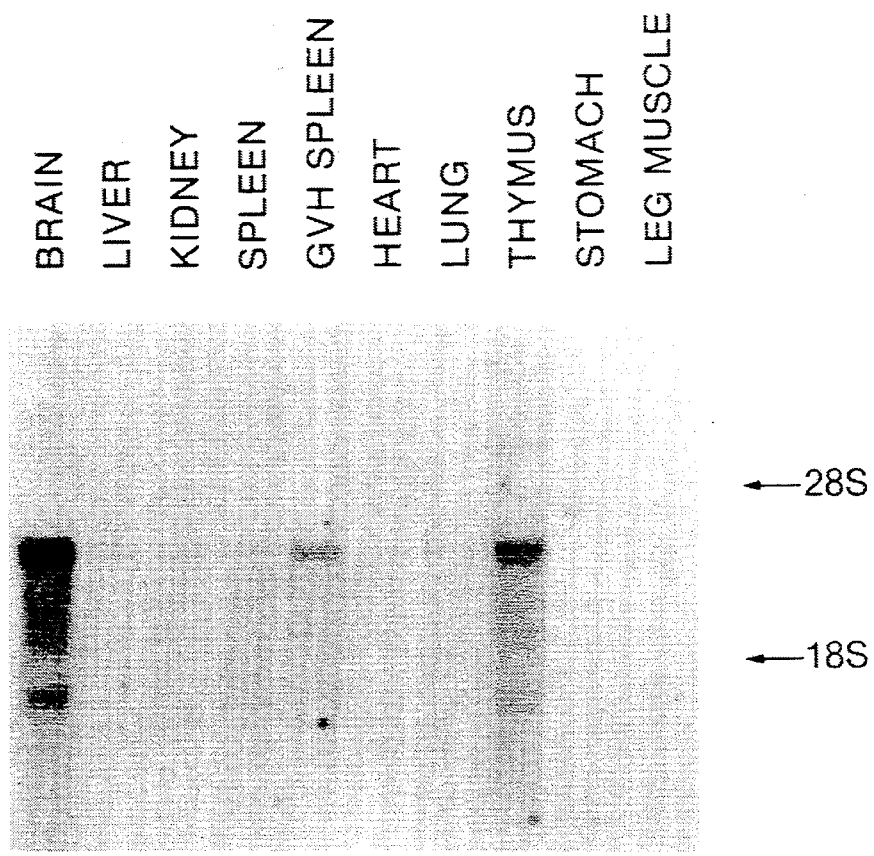
FIG. 11. Northern analysis of Glvr-1 in mouse tissues.

FIG. 11 shows that, using pMGR1 as probe, a single RNA species is readily detected in most tissues. Longer exposures allows detection of this RNA in all tissues examined except perhaps stomach. Despite the widespread presence of the RNA, there is considerable variation in level between tissues. The brain contains by far the highest levels, being several-fold higher than the next highest tissue, which is thymus. Spleen undergoing a graft-versus-host reaction (in which 60% of the cells are activated donor T cells) has a level of RNA approaching that found in the thymus.

Figure 12:
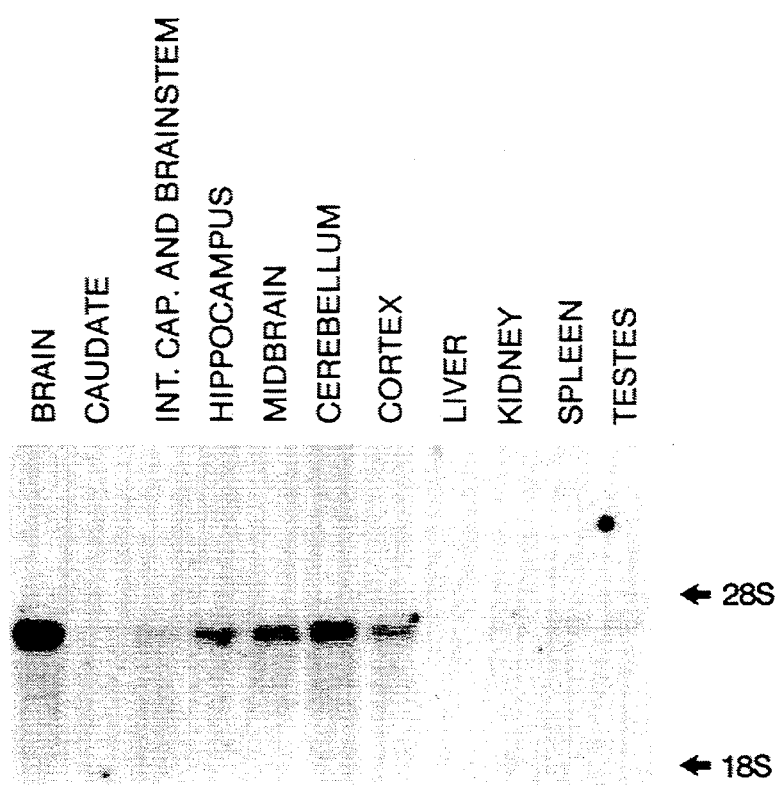
FIG. 12. Northern Analysis of Glvr-1 in rat tissues. Total brain was derived from a single rat. All compartments of brain were also derived from a single rat.

To determine which portion of brain expresses high levels of RNA, all compartments of brain are analyzed individually. FIG. 12 shows that the RNA is found at a high level in rat brain in comparison to other tissues, mirroring the results found with mouse tissues. Within the brain, RNA levels are found to be high in most compartments, notably so in hippocampus, midbrain, cerebellum, and cortex. The caudate nucleus, in contrast, expresses low levels of Glvr-1 RNA.

Figure 13:
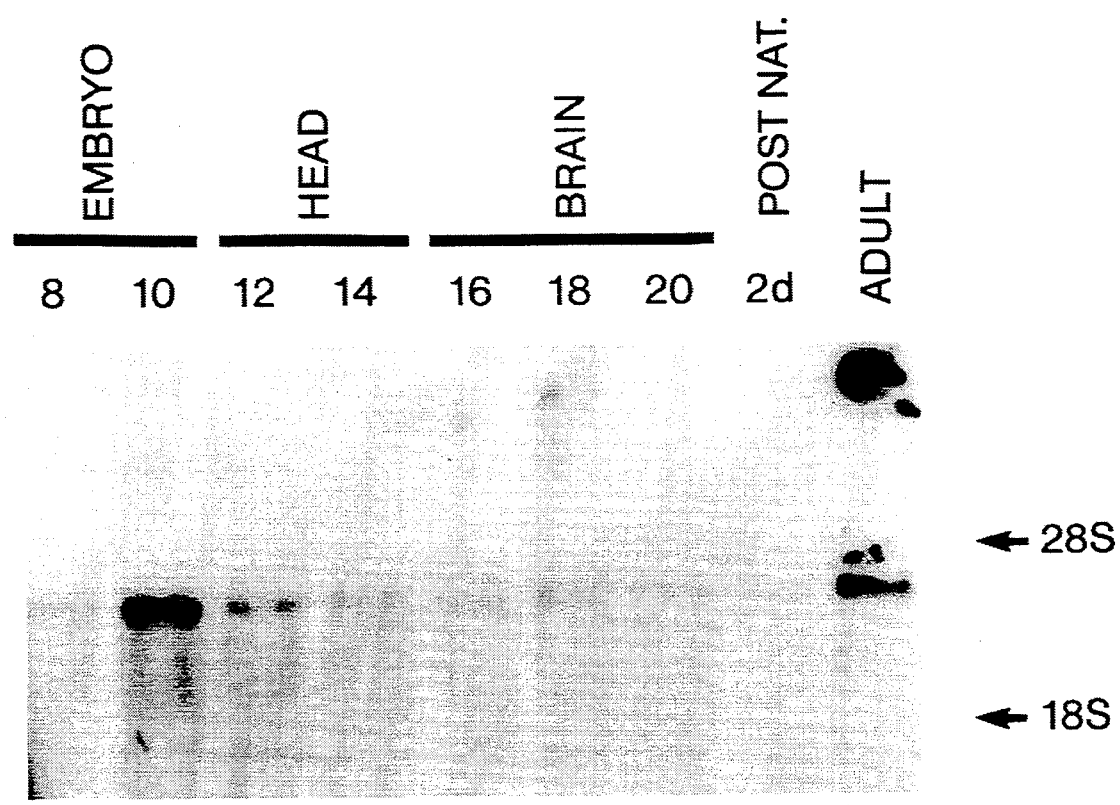
FIG. 13. Northern analysis of Glvr-1 in tissues of the rat taken at various stages of development. Whole embryos, heads, or brains were taken at the indicated days. Adult brain was from a 2-month-old rat.

In order to examine Glvr-1 expression during development, RNA levels are analyzed at several stages of rat embryogenesis. As can be seen in FIG. 13, the RNA is expressed at day 10 much more abundantly than at day 8 of development of whole rat embryos. No fluctuation is found when whole heads are analyzed at days 12 and 14, nor (except for a gradual decline) when whole brains are taken at days 16, 18, and 20 and two days after birth. A higher level of RNA is found in 2-month-old adult brain as compared to the later stages during embryogenesis.

BIBLIOGRAPHY

Glisin, V.; Crkvenjov, R.; and Byus, C. Ribonucleic acid isolated by cesium chloride centrifugation. *Biochemistry*, 13:2633–2639 (1974).

Haapala, D. K.; Robey, W. G.; Oroszlan, S. D.; and Tsai, W. P. Isolation from cats of an endogenous type C virus with a novel envelope glycoprotein. *J. Virol*, 53:827–833 (1985).

Ishikawa, H.; Hind, T.; Kato, H.; Suzuki, H.; and Saito, K. Cytotoxic T lymphocyte response to minor alloantigen in H-42b mice; clonal inactivation of the precursor cytotoxic T lymphocytes by veto-like spleen cells that express the H-42a antigen. *J. Immunol* 137:2080–2088 (1986).

Kaelbling, M.; Eddy, R.; Shows, T. B.; Copeland, N. G.; Gilbert, D. J.; Jenkins, M. A.; Klinger, H. P.; and O'Hara, B. Localization of the human gene allowing infection by gibbon age leukemia virus to human chromosome region 2q11-q 14 and to the homologous region on mouse chromosome 2. *J. Virol*, in press (1991).

Kozak, M. Point mutations define a sequence flanking the AUG initiator codon that modulates translation by eukaryotic ribosomes. *Cell*, 44:283–292 (1986).

Kurtz, M. E.; Craff, R. J.; Adelman, A.; Martin-Morgan, D.; and Click, R. E. CTL and serologically defined antigens of the B2M, H-3 region. *J. Immunol* 135:2847–2852 (1985).

Kyte, J. and Doolittle, R. F. A simple method for displaying the hydropathic character of a protein. *Journal of Molecular Biology*, 157:105–132 (1982).

Maddon, P. J.; Dalgleish, A. G.; McDougal, J. S.; Clapham, P. R.; Weiss, R. A.; and Axel, R. The T4 gene encodes the AIDS virus receptor and is expressed in the immune system and the brain. *Cell*, 47:333–348 (1986).

McDougal, J. S.; Kennedy, M. S.; Sligh, J. M.; Cort, S. P.; Mawle, A.; and Nicholson, J. K. A. Binding of HTLV-III/LAV to T4+ cells by a complex of the 110K viral protein and the Tf molecule. *Science*, 231:382–385 (1986).

Mulligan, R. C. and Berg, P. *Proceedings of the National Academy of Sciences*, U.S.A., 78:2072–2076 (1981).

Needleman, S. and Wunsch, C. J. A general method applicable to the search for similarity in the amino acid sequence in two proteins *Mol. Biol.*, 48:443–453 (1970).

Noda, T. M.; Satake, M.; Robins, T.; and Ito, Y. Isolation and characterization of NIH3T3 cells expressing polyoma small T antigen. *Journal of Virology*, 60:105–113 (1986).

O'Hara, B.; Johann, S. V.; Klinger, H. P.; Blair, D. G.; Rubinson, H.; Dunn, K. J.; Sass, P.; Vitek, S. M.; and Robins, T. Characterization of a human gene conferring sensitivity to infection by gibbon ape leukemia virus. *Cell Growth Differ.*, 3:119–127 (1990).

O'Hara, B.; Klinger, H. P.; Curran, T.; Zhang, Y.; and Blair, D. G. *Molecular and Cellular Biology*, 7:2941–2946 (1987).

Sanger, F.; Nicklen, S.; and Coulson, A. R. DNA-sequencing with chain-terminating inhibitors. *Proc. Nationals Academy of Science*, U.S.A., 74:5463–5467 (1977).

Southern, P. J. and Berg, P. *Journal of Molecular and Applied Genetics*, 1:327–351 (1982).

Vieira, J. and Messing, J. Production of single-stranded plasmid DNA. *Methods Enzymol.*, 153:3–11 (1987).

Weiss, R. N.; Teich, N.; Varmus, H.; Coffin, J. RNA Tumor Viruses: *Molecular Biology of Tumor Viruses*, Second Edition, Volume 1. Cold Spring Harbor Laboratories, Cold Spring Harbor (1984).

---

What is claimed is:

1. The purified isolated DNA sequence encoding for GALV receptor protein defined in SEQ. I.D. NO. 1 or 3.

2. The purified isolated DNA sequence according to claim 1, encoding for the GALV receptor protein defined in SEQ. I.D. NO. 2 wherein said GALV receptor protein is derived from a species selected from the group consisting of human, mouse, dog or cat.

* * * * *

SEQUENCE LISTING ( 1 ) GENERAL INFORMATION:

( i i i ) NUMBER OF SEQUENCES: 3

( 2 ) INFORMATION FOR SEQ ID NO: 1:

( i ) SEQUENCE CHARACTERISTICS:
      ( A ) LENGTH: 3211 Base Pairs
      ( B ) TYPE: Nucleotide Sequence
      ( C ) STRANDEDNESS: Single
      ( D ) TOPOLOGY: Linear ( i i ) MOLECULE TYPE: DNA ( x i ) SEQUENCE DESCRIPTION: SEQ ID NO: 1:

```
GAGCTGTCCC  CGGTGCCGCC  GACCCGGGCC  GTGCCGTGTG         40

CCCGTGGCTC  CAGCCGCTGC  CGCCTCGATC  TCCTCGTCTC         80

CCGCTCCGCC  CTCCCTTTTC  CCTGGATGAA  CTTGCGTCCT        120

TTCTCTTCTC  CGCCATGGAA  TTCTGCTCCG  TGCTTTTAGC        160

CCTCCTGAGC  CAAAGAAACC  CCAGACAACA  GATGCCCATA        200

CGCAGCGTAT  AGCAGTAACT  CCCCAGCTCG  GTTTCTGTGC        240

CGTAGTTTAC  AGTATTTAAT  TTTATATAAT  ATATATTATT        280

TATTATAGCA  TTTTTGATAC  CTCATATTCT  GTTTACACAT        320
```

| | |
|---|---|
| CTTGAAAGGC GCTCAGTAGT TCTCTTACTA AACAACCACT | 360 |
| ACTCCAGAGA | 370 |
| ATG GCA ACG CTG ATT ACC AGT ACT ACA GCT GCT | 403 |
| ACC GCC GCT TCT GGT CCT TTG GTG GAC TAC CTA | 436 |
| TGG ATG CTC ATC CTG GGC TTC ATT ATT GCA TTT | 469 |
| GTC TTG GCA TTC TCC GTG GGA GCC AAT GAT GTA | 502 |
| GCA AAT TCT TTT GGT ACA GCT GTG GGC TCA GGT | 535 |
| GTA GTG ACC CTG AAG CAA GCC TGC ATC CTA GCT | 568 |
| AGC ATC TTT GAA ACA GTG GGC TCT GTC TTA CTG | 601 |
| GGG GCC AAA GTG AGC GAA ACC ATC CGG AAG GGC | 634 |
| TTG ATT GAC GTG GAG ATG TAC AAC TCG ACT CAA | 667 |
| GGG CTA CTG ATG GCC GGC TCA GTC AGT GCT ATG | 700 |
| TTT GGT TCT GCT GTG TGG CAA CTC GTG GCT TCG | 733 |
| TTT TTG AAG CTC CCT ATT TCT GGA ACC CAT TGT | 766 |
| ATT GTT GGT GCA ACT ATT GGT TTC TCC CTC GTG | 799 |
| GCA AAG GGG CAG GAG GGT GTC AAG TGG TCT GAA | 832 |
| CTG ATA AAA ATT GTG ATG TCT TGG TTC GTG TCC | 865 |
| CCA CTG CTT TCT GGA ATT ATG TCT GGA ATT TTA | 898 |
| TTC TTC CTG GTT CGT GCA TTC ATC CTC CAT AAG | 931 |
| GCA GAT CCA GTT CCT AAT GGT TTG CGA GCT TTG | 964 |
| CCA GTT TTC TAT GCC TGC ACA GTT GGA ATA AAC | 997 |
| CTC TTT TCC ATC ATG TAT ACT GGA GCA CCG TTG | 1030 |
| CTG GGC TTT GAC AAA CTT CCT CTG TGG GGT ACC | 1063 |
| ATC CTC ATC TCG GTG GGA TGT GCA GTT TTC TGT | 1096 |
| GCC CTT ATC GTC TGG TTC TTT GTA TGT CCC AGG | 1129 |
| ATG AAG AGA AAA ATT GAA CGA GAA ATA AAG TGT | 1162 |
| AGT CCT TCT GAA AGC CCC TTA ATG GAA AAA AAG | 1195 |
| AAT AGC TTG AAA GAA GAC CAT GAA GAA ACA AAG | 1228 |
| TTG TCT GTT GGT GAT ATT GAA AAC AAC CAT CCT | 1261 |
| GTT TCT GAG GTA GGG CCT GCC ACT GTG CCC CTC | 1294 |
| CAG GCT GTG GTG GAG GAG AGA ACA GTC TCA TTC | 1327 |
| AAA CTT GGA GAT TTG GAG GAA GCT CCA GAG AGA | 1360 |
| GAG AGG CTT CCC AGC GTG GAC TTG AAA GAG AA | 1393 |
| ACC AGC ATA GAT AGC ACC GTG AAT GGT GCA GTG | 1426 |
| CAG TTG CCT AAT GGG AAC CTT GTC CAG TTC ACT | 1459 |
| CAA GCC GTC AGC AAC CAA ATA AAC TCC AGT GGC | 1492 |
| CAC TCC CAG TAT CAC ACC GTG CAT AAG GAT TCC | 1525 |
| GGC CTG TAC AAA GAG CTA CTC CAT AAA TTA CAT | 1558 |
| CTT GCC AAG GTG GGA GAT TGC ATG GGA GAC TCC | 1591 |
| GGT GAC AAA CCC TTA AGG CGC AAT AAT AGC TAT | 1624 |
| ACT TCC TAT ACC ATG GCA ATA TGT GGC ATG CCT | 1657 |

| | |
|---|---|
| CTG GAT TCA TTC CGT GCC AAA GAA GGT GAA CAG | 1690 |
| AAG GGC GAA GAA ATG GAG AAG CTG ACA TGG CCT | 1723 |
| AAT GCA GAC TCC AAG AAG CGA ATT CGA ATG GAC | 1756 |
| AGT TAC ACC AGT TAC TGC AAT GCT GTG TCT GAC | 1789 |
| CTT CAC TCA GCA TCT GAG ATA GAC ATG AGT GTC | 1822 |
| AAG GCA GCG ATG GGT CTA GGT GAC AGA AAA GGA | 1855 |
| AGT AAT GGC TCT CTA GAA GAA TGG TAT GAC CAG | 1888 |
| GAT AAG CCT GAA GTC TCT CTC CTC TTC CAG TTC | 1921 |
| CTG CAG ATC CTT ACA GCC TGC TTT GGG TCA TTC | 1954 |
| GCC CAT GGT GGC AAT GAC GTA AGC AAT GCC ATT | 1987 |
| GGG CCT CTG GTT GCT TTA TAT TTG GTT TAT GAC | 2020 |
| ACA GGA GAT GTT TCT TCA AAA GTG GCA ACA CCA | 2053 |
| ATA TGG CTT CTA CTC TAT GGT GGT GTT GGT ATC | 2086 |
| TGT GTT GGT CTG TGG GTT TGG GGA AGA AGA GTT | 2119 |
| ATC CAG ACC ATG GGG AAG GAT CTG ACA CCG ATC | 2152 |
| ACA CCC TCT AGT GGC TTC AGT ATT GAA CTG GCA | 2185 |
| TCT GCC CTC ACT GTG GTG ATT GCA TCA AAT ATT | 2218 |
| GGC CTT CCC ATC AGT ACA ACA CAT GTG AAA GTG | 2251 |
| GGC TCT GTT GTG TCT GTT GGC TGG CTC CGG TCC | 2284 |
| AAG AAG GCT GTT GAC TGG CGT CTC TTT CGT AAC | 2317 |
| ATT TTT ATG GCC TGG TTT GTC ACA GTC CCC ATT | 2350 |
| TCT GGA GTT ATC AGT GCT GCC ATC ATG GCA ATC | 2383 |
| TTC AGA TAT GTC ATC CTC AGA ATG TGA | 2410 |
| AGCTGTTTGA GATTAAAATT TGTGTCAATG TTTGGGACCA | 2450 |
| TCTTAGGTAT TCCTGCTCCC CTGAAGAATG ATTACAGTGT | 2490 |
| TAACAGAAGA CTGACAAGAG TCTTTTTATT TGGGAGCAGA | 2530 |
| GGAGGGAAGT GTTACTTGTG CTATAACTGC TTTTGTGCTA | 2570 |
| AATATGAATT GTCTCAAAAT TAGCTGTGTA AAATAGCCCG | 2610 |
| GGTTCCACTG GCTCCTGCTG AGGTCCCCTT TCCTTCTGGG | 2650 |
| CTGTGAATTC CTGTACATAT TTCTCTACTT TTTGTATCAG | 2690 |
| GCTTCAATTC CATTATGTTT TAATGTTGTC TCTGAAGATG | 2730 |
| ACTTGTGATT TTTTTTCTT TTTTTAAAC CATGAAGAGC | 2770 |
| CGTTTGACAG AGCATGCTCT GCGTTGTTGG TTTCACCAGC | 2810 |
| TTCTGCCCTC ACATGCACAG GGATTTAACA ACAAAAATAT | 2850 |
| AACTACAACT TCCCTTGTAG TCTCTTATAT AAGTAGAGTC | 2890 |
| CTTGGTACTC TGCCCTCCTG TCAGTAGTGG CAGGATCTAT | 2930 |
| TGGCATATTC GGGAGCTTCT TAGAGGGATG AGGTTCTTTG | 2970 |
| AACACAGTGA AAATTTAAAT TAGTAACTTT TTTGCAAGCA | 3010 |
| GTTTATTGAC TGTTATTGCT AAGAAGAAGT AAGAAAGAAA | 3050 |
| AAGCCTGTTG GCAATCTTGG TTATTTCTTT AAGATTTCTG | 3090 |
| GCAGTGTGGG ATGGATGAAT GAAGTGGAAT GTGAACTTTG | 3130 |

| | |
|---|---|
| GGCAAGTTAA ATGGGACAGC CTTCCATGTT CATTTGTCTA | 3170 |
| CCTCTTAACT GAATAAAAAA GCCTACAGTT TTTAGAAAAA | 3210 |
| A | 3211 |

( 3 ) INFORMATION FOR SEQ ID NO: 2:

( i ) SEQUENCE CHARACTERISTICS:
        ( A ) LENGTH: 680 Amino Acid Residues
        ( B ) TYPE: Amino Acid Sequence
        ( C ) STRANDEDNESS: Single
        ( D ) TOPOLOGY: Linear ( i i ) MOLECULE TYPE: Protein ( x i ) SEQUENCE DESCRIPTION: SEQ ID NO: 2:

```
Met Ala Thr Leu Ile Thr Ser Thr Thr Ala
 1               5                   10

Thr Ala Ala Ser Gly Pro Leu Val Asp Tyr Leu
             15                  20

Trp Met Leu Ile Leu Gly Phe Ile Ala Phe
         25                  30

Val Leu Ala Phe Ser Val Gly Ala Asn Asp Val
     35                  40

Ala Asn Ser Phe Gly Thr Ala Val Gly Ser Gly
 45                  50                   55

Val Val Thr Leu Lys Gln Ala Cys Ile Leu Ala
                 60                  65

Ser Ile Phe Glu Thr Val Gly Ser Val Leu Leu
             70                  75

Gly Ala Lys Val Ser Glu Thr Ile Arg Lys Gly
         80                  85

Leu Ile Asp Val Glu Met Tyr Asn Ser Thr Gln
     90                  85

Gly Leu Leu Met Ala Gly Ser Val Ser Ala Met
100                 105                  110

Phe Gly Ser Ala Val Trp Gln Leu Val Ala Ser
                115                  120

Phe Leu Lys Leu Pro Ile Ser Gly Thr His Cys
             125                 130

Ile Val Gly Ala Thr Ile Gly Phe Ser Leu Val
         135                 140

Ala Lys Gly Gln Glu Gly Val Lys Trp Ser Glu
     145                 150

Leu Ile Lys Ile Val Met Ser Trp Phe Val Ser
155                 160                  165

Pro Leu Leu Ser Gly Ile Met Ser Gly Ile Leu
                170                  175

Phe Phe Leu Val Arg Ala Phe Ile Leu His Lys
             180                 185

Ala Asp Pro Val Pro Asn Gly Leu Arg Ala Leu
     190                 195

Pro Val Phe Tyr Ala Cys Thr Val Gly Ile Asn
200                 205

Leu Phe Ser Ile Met Tyr Thr Gly Ala Pro Leu
210                 215                  220

Leu Gly Phe Asp Lys Leu Pro Leu Trp Gly Thr
             225                 230
```

```
Ile  Leu  Ile  Ser  Val  Gly  Cys  Ala  Val  Phe  Cys
               235                      240

Ala  Leu  Ile  Val  Trp  Phe  Phe  Val  Cys  Pro  Arg
               245                 250

Met  Lys  Arg  Lys  Ile  Glu  Arg  Glu  Ile  Lys  Cys
          255                 260

Ser  Pro  Ser  Glu  Ser  Pro  Leu  Met  Glu  Lys  Lys
265                      270                      275

Asn  Ser  Leu  Lys  Glu  Asp  His  Glu  Glu  Thr  Lys
               280                      285

Leu  Ser  Val  Gly  Asp  Ile  Glu  Asn  Lys  His  Pro
               290                 295

Val  Ser  Glu  Val  Gly  Pro  Ala  Thr  Val  Pro  Leu
          300                      305

Gln  Ala  Val  Val  Glu  Glu  Arg  Thr  Val  Ser  Phe
          310                      315

Lys  Leu  Gly  Asp  Leu  Glu  Glu  Ala  Pro  Glu  Arg
320                      325                      330

Glu  Arg  Leu  Pro  Ser  Val  Asp  Leu  Lys  Glu  Glu
               335                      340

Thr  Ser  Ile  Asp  Ser  Thr  Val  Asn  Gly  Ala  Val
               345                      350

Gln  Leu  Pro  Asn  Gly  Asn  Leu  Val  Gln  Phe  Ser
               355                 360

Gln  Ala  Val  Ser  Asn  Gln  Ile  Asn  Ser  Ser  Gly
          365                 370

His  Ser  Gln  Tyr  His  Thr  Val  His  Lys  Asp  Ser
375                      380                      385

Gly  Leu  Tyr  Lys  Glu  Leu  Leu  His  Lys  Leu  His
               390                      395

Leu  Ala  Lys  Val  Gly  Asp  Cys  Met  Gly  Asp  Ser
               400                      405

Gly  Asp  Lys  Pro  Leu  Arg  Arg  Asn  Asn  Ser  Tyr
          410                      415

Thr  Ser  Tyr  Thr  Met  Ala  Ile  Cys  Gly  Met  Pro
          420                      425

Leu  Asp  Ser  Phe  Arg  Ala  Lys  Glu  Gly  Glu  Gln
430                      435                      440

Lys  Gly  Glu  Glu  Met  Glu  Lys  Leu  Thr  Trp  Pro
               445                      450

Asn  Ala  Asp  Ser  Lys  Lys  Arg  Ile  Arg  Met  Asp
               455                      460

Ser  Tyr  Thr  Ser  Tyr  Cys  Asn  Ala  Val  Ser  Asp
          465                      470

Leu  His  Ser  Ala  Ser  Glu  Ile  Asp  Met  Ser  Val
          475                      480

Lys  Ala  Ala  Met  Gly  Leu  Gly  Asp  Arg  Lys  Gly
485                      490                      495

Ser  Asn  Gly  Ser  Leu  Glu  Glu  Trp  Tyr  Asp  Gln
                    500                 505

Asp  Lys  Pro  Glu  Val  Ser  Leu  Leu  Phe  Gln  Phe
               510                      515

Leu  Gln  Ile  Leu  Thr  Ala  Cys  Phe  Gly  Ser  Phe
          520                      525

Ala  His  Gly  Gly  Asn  Asp  Val  Ser  Asn  Ala  Ile
```

```
           530                         535
Gly  Pro  Leu  Val  Ala  Leu  Tyr  Leu  Val  Tyr  Asp
540                      545                      550

Thr  Gly  Asp  Val  Ser  Ser  Lys  Val  Ala  Thr  Pro
                    555                      560

Ile  Trp  Leu  Leu  Leu  Tyr  Gly  Gly  Val  Gly  Ile
               565                      570

Cys  Val  Gly  Leu  Trp  Val  Trp  Gly  Arg  Arg  Val
          575                      580

Ile  Gln  Thr  Met  Gly  Lys  Asp  Leu  Thr  Pro  Ile
     585                      590

Thr  Pro  Ser  Ser  Gly  Phe  Ser  Ile  Glu  Leu  Ala
595                      600                      605

Ser  Ala  Leu  Thr  Val  Val  Ile  Ala  Ser  Asn  Ile
               610                      615

Gly  Leu  Pro  Ile  Ser  Thr  Thr  His  Cys  Lys  Val
               620                      625

Gly  Ser  Val  Val  Ser  Val  Gly  Trp  Leu  Arg  Ser
          630                      635

Lys  Lys  Ala  Val  Asp  Trp  Arg  Leu  Phe  Arg  Asn
     640                      645

Ile  Phe  Met  Ala  Trp  Phe  Val  Thr  Val  Pro  Ile
650                      655                      660

Ser  Gly  Val  Ile  Ser  Ala  Ala  Ile  Met  Ala  Ile
                    665                      670

Phe  Arg  Tyr  Val  Ile  Leu  Arg  Met  Xaa
               675                      680
```

( 4 ) INFORMATION FOR SEQ ID NO: 3:

( i ) SEQUENCE CHARACTERISTICS:
        ( A ) LENGTH: 3260 BPs 681 Amino Acid Residues
        ( B ) TYPE: Nucleotide and Amino Acid Sequences
        ( C ) STRANDEDNESS: Single
        ( D ) TOPOLOGY: Linear ( i i ) MOLECULE TYPE: DNA and Protein ( x i ) SEQUENCE DESCRIPTION: SEQ ID NO: 3:

```
GACGGTATCG ATAAGCTTGA TATCGAATTC CCTGTGCTCC            40

ACCTTGCACA GCGTTTGGGG GACTGAAGAC ATAAGTGACG            80

GGCGGGGGGG GGGGGGACTA TGCGGAGTCC CAGGCTGCCC           120

TCTTCCCAGA GATGCGCCGC TATTGTTATT TTCTTCCACT           160

TCGTCCCCCC AGGATGAACT TGCGTCCTTT CTCTAATCCG           200

CCATGGAATT CTGCTCCGTG CTTTTAGCCC TCCAGAGCCA           240

AAGAAACCCC AGACAACAGA CGCCCAGACG CAGCAGCGTA           280

TAGCAGTAAC TCCCCAGCTC GGTTTCCGTG CCGTAGTTTA           320

CAGTATTTAA TTTTATATAA TATATACTAT TTATTATAGC           360

ATTTTGATAC CTCATTCCGT TTACACATCT CAAAAGCCGC           400

TTAGTAATTC TCTTATTATT TAAAGAACCA CTACACTAGA           440

GA                                                    442

ATG GAA TCT ACT GTG GCA ACG ATT ACT AGT ACC CTA       478
Met Glu Ser Thr Val Ala Thr Ile Thr Ser Thr Leu
 1               5                  10
```

| | | | | | | | | | | | |
|---|---|---|---|---|---|---|---|---|---|---|---|
| GCT | GCT | GTT | ACT | GCT | TCC | GCT | CCA | CCG | AAG | TAT | GAC | 514 |
| Ala | Ala | Val | Thr | Ala | Ser | Ala | Pro | Pro | Lys | Tyr | Asp |
| | | 15 | | | | | 20 | | | | |
| AAT | CTA | TGG | ATG | CTC | ATC | CTG | GGC | TTC | ATC | ATT | GCA | 550 |
| Asn | Leu | Trp | Met | Leu | Ile | Leu | Gly | Phe | Ile | Ile | Ala |
| 25 | | | | 30 | | | | | 35 | | |
| TTT | GTC | TTG | GCA | TTC | TCC | GTG | GGA | GCC | AAT | GAT | GTA | 586 |
| Phe | Val | Leu | Ala | Phe | Ser | Val | Gly | Ala | Asn | Asp | Val |
| | | | 40 | | | | | 45 | | | |
| GCA | AAT | TCG | TTC | GGT | ACA | GCT | GTA | GGC | TCA | GGT | GTA | 622 |
| Ala | Asn | Ser | Phe | Gly | Thr | Ala | Val | Gly | Ser | Gly | Val |
| | 50 | | | | | 55 | | | | | 60 |
| GTG | ACC | CTG | AAG | CAA | GCC | TGC | ATC | TTA | GCT | AGC | ATC | 658 |
| Val | Thr | Leu | Lys | Gln | Ala | Cys | Ile | Leu | Ala | Ser | Ile |
| | | | | 65 | | | | | 70 | | |
| TTC | GAA | ACT | GTG | GGC | TCC | GCC | TTG | CTG | GGG | GCC | AAA | 694 |
| Phe | Glu | Thr | Val | Gly | Ser | Ala | Leu | Leu | Gly | Ala | Lys |
| | | 75 | | | | | 80 | | | | |
| GTG | AGC | GAA | ACC | ATC | CGG | AAC | GGC | TTG | ATA | GAT | GTG | 730 |
| Val | Ser | Glu | Thr | Ile | Arg | Asn | Gly | Leu | Ile | Asp | Val |
| 85 | | | | | 90 | | | | | 95 | |
| GAG | CTG | TAC | AAC | GAA | ACT | CAA | GAT | CTG | CTC | ATG | GCT | 766 |
| Glu | Leu | Tyr | Asn | Glu | Thr | Gln | Asp | Leu | Leu | Met | Ala |
| | | | 100 | | | | | 105 | | | |
| GGC | TCC | GTC | AGT | GCT | ATG | TTT | GGT | TCT | GCT | GTG | TGG | 802 |
| Gly | Ser | Val | Ser | Ala | Met | Phe | Gly | Ser | Ala | Val | Trp |
| | 110 | | | | | 115 | | | | | 120 |
| CAG | CTC | GTG | GCT | TCG | TTT | TTG | AAG | CTT | CCG | ATT | TCT | 838 |
| Gln | Leu | Val | Ala | Ser | Phe | Leu | Lys | Leu | Pro | Ile | Ser |
| | | | | 125 | | | | | 130 | | |
| GGG | ACC | CAT | TGT | ATT | GTC | GGT | GCA | ACC | ATT | GGT | TTC | 874 |
| Gly | Thr | His | Cys | Ile | Val | Gly | Ala | Thr | Ile | Gly | Phe |
| | | 135 | | | | | 140 | | | | |
| TCC | CTT | GTG | GCA | AAT | GGG | CAG | AAG | GGT | GTC | AAG | TGG | 910 |
| Ser | Leu | Val | Ala | Asn | Gly | Gln | Lys | Gly | Val | Lys | Trp |
| 145 | | | | | 150 | | | | | 160 | |
| TCT | GAA | CTG | ATA | AAA | ATT | GTG | ATG | TCG | TGG | TTC | GTC | 946 |
| Ser | Glu | Leu | Ile | Lys | Ile | Val | Met | Ser | Trp | Phe | Val |
| | | | 160 | | | | | 165 | | | |
| TCT | CCG | CTG | CTT | TCT | GGT | ATT | ATG | TCT | GGA | ATT | TTA | 982 |
| Ser | Pro | Leu | Leu | Ser | Gly | Ile | Met | Ser | Gly | Ile | Leu |
| | 170 | | | | | 175 | | | | | 180 |
| TTC | TTC | CTT | GTT | CGT | GCG | TTC | ATC | CTC | CGT | AAG | GCA | 1018 |
| Phe | Phe | Leu | Val | Arg | Ala | Phe | Ile | Leu | Arg | Lys | Ala |
| | | | | 185 | | | | | 190 | | |
| GAT | CCG | GTT | CCT | AAT | GGC | TTA | CGA | GCT | TTA | CCA | ATT | 1054 |
| Asp | Pro | Val | Pro | Asn | Gly | Leu | Arg | Ala | Leu | Pro | Ile |
| | | 195 | | | | | 200 | | | | |
| TTT | TAT | GCC | TGC | ACA | ATC | GGA | ATC | AAC | CTC | TTT | TCC | 1090 |
| Phe | Tyr | Ala | Cys | Thr | Ile | Gly | Ile | Asn | Leu | Phe | Ser |
| 205 | | | | | 210 | | | | | 215 | |
| ATT | ATG | TAT | ACT | GGA | GCA | CCG | TTG | CTG | GGC | TTT | GAC | 1126 |
| Ile | Met | Tyr | Thr | Gly | Ala | Pro | Leu | Leu | Gly | Phe | Asp |
| | | | 220 | | | | | 225 | | | |
| AAA | CTT | CCT | CTG | TGG | GGT | ACC | ATC | CTC | ATC | TCG | GTG | 1162 |
| Lys | Leu | Pro | Leu | Trp | Gly | Thr | Ile | Leu | Ile | Ser | Val |
| | | 230 | | | | | 235 | | | | 240 |
| GGA | TGT | GCA | GTT | TTC | TGT | GCC | CTT | ATC | GTC | TGG | TTC | 1198 |
| Gly | Cys | Ala | Val | Phe | Cys | Ala | Leu | Ile | Val | Trp | Phe |
| | | | | 245 | | | | | 250 | | |
| TTT | GTA | TGT | CCC | AGG | ATG | AAG | AGA | AAA | ATT | GAA | CGA | 1234 |
| Phe | Val | Cys | Pro | Arg | Met | Lys | Arg | Lys | Ile | Glu | Arg |

```
                    255                          260
GAA GTA AAG TCT AGT CCG TCT GAA AGT CCC TTA ATG      1270
Glu Val Lys Ser Ser Pro Ser Glu Ser Pro Leu Met
265             270                 275

GAA AAG AAG AGC AAC TTA AAA GAA GAC CAT GAA GAA      1306
Glu Lys Lys Ser Asn Leu Lys Glu Asp His Glu Glu
            280                 285

ACA AAG ATG GCT CCT GGA GAC GTT GAG CAT AGG AAT      1342
Thr Lys Met Ala Pro Gly Asp Val Glu His Arg Asn
290             295                 300

CCT GTG TCT GAG GTA GTG TGT GCC ACT GGG CCA CTC      1378
Pro Val Ser Glu Val Val Cys Ala Thr Gly Pro Leu
                305                 310

CGG GCT GTG GTG GAG GAG AGG ACG GTG TCA TTC AAA      1414
Arg Ala Val Val Glu Glu Arg Thr Val Ser Phe Lys
        315                 320

CTT GGT GAC CTG GAG GAG GCT CCG GAG CGA GAG CGG      1450
Leu Gly Asp Leu Glu Glu Ala Pro Glu Arg Glu Arg
325             330                 335

CTT CCC ATG GAC CTG AAG GAG GAG ACC AGC ATA GAC      1486
Leu Pro Met Asp Leu Lys Glu Glu Thr Ser Ile Asp
            340                 345

AGC ACC ATC AAT GGT GCA GTG CAG TTG CCT AAT GGG      1522
Ser Thr Ile Asn Gly Ala Val Gln Leu Pro Asn Gly
350             355                 360

AAC CTT GTT CAG TTC AGT CAA ACT GTC AGC AAC CAG      1558
Asn Leu Val Gln Phe Ser Gln Thr Val Ser Asn Gln
                365                 370

ATC AAC TCC AGT GGC CAC TAT CAG TAT CAC ACC GTG      1594
Ile Asn Ser Ser Gly His Tyr Gln Tyr His Thr Val
        375                 380

CAC AAG GAT TCT GGC TTG TAC AAG GAG CTG CTC CAT      1630
His Lys Asp Ser Gly Leu Tyr Lys Glu Leu Leu His
385             390                 395

AAG TTA CAT CTG GCC AAG GTG GGA GAC TGC ATG GGA      1666
Lys Leu His Leu Ala Lys Val Gly Asp Cys Met Gly
            400                 405

GAT TCT GGG GAC AAG CCC TTG AGA CGC AAC AAC AGC      1702
Asp Ser Gly Asp Lys Pro Leu Arg Arg Asn Asn Ser
410             415                 420

TAC ACT TCC TAC ACT ATG GCA ATA TGT GGC ATG CCC      1738
Tyr Thr Ser Tyr Thr Met Ala Ile Cys Gly Met Pro
                425                 430

CTG GAT TCA TTC CGT GCC AAA GAA GGT GAA CAA AAG      1774
Leu Asp Ser Phe Arg Ala Lys Glu Gly Glu Gln Lys
        435                 440

GGA GAT GAA ATG GAG ACG CTG ACA TGG CCT AAT GCA      1810
Gly Asp Glu Met Glu Thr Leu Thr Trp Pro Asn Ala
445             450                 455

GAT ACC AAG AAG CGG ATT CGA ATG GAC AGT TAC ACC      1846
Asp Thr Lys Lys Arg Ile Arg Met Asp Ser Tyr Thr
            460                 465

AGT TAC TGC AAT GCC GTG TCT GAC CTT CAC TCC GAG      1882
Ser Tyr Cys Asn Ala Val Ser Asp Leu His Ser Glu
470             475                 480

TCT GAG ATG GAC ATG AGT GTG AAG GCT GAG ATG GGC      1918
Ser Glu Met Asp Met Ser Val Lys Ala Glu Met Gly
                485                 490

CTG GGT GAC AGA AAA GGA AGC AGT GGC TCT CTT GAA      1954
Leu Gly Asp Arg Lys Gly Ser Ser Gly Ser Leu Glu
        495                 500
```

| | | | | | | | | | | | |
|---|---|---|---|---|---|---|---|---|---|---|---|
| GAA | TGG | TAT | GAC | CAG | GAT | AAG | CCT | GAA | GTG | TCC | CTT | 1990 |
| Glu | Trp | Tyr | Asp | Gln | Asp | Lys | Pro | Glu | Val | Ser | Leu | |
| 505 | | | | 510 | | | | | | 515 | | |
| CTC | TTC | CAG | TTC | CTG | CAG | ATC | CTT | ACA | GCC | TGC | TTT | 2026 |
| Leu | Phe | Gln | Phe | Leu | Gln | Ile | Leu | Thr | Ala | Cys | Phe | |
| | | 520 | | | | | 525 | | | | | |
| GGG | TCA | TTT | GCC | CAT | GGT | GGC | AAT | GAC | GTC | AGC | AAT | 2062 |
| Gly | Ser | Phe | Ala | His | Gly | Gly | Asn | Asp | Val | Ser | Asn | |
| | 530 | | | | 535 | | | | | | 540 | |
| GCC | ATC | GGC | CCT | CTG | GTT | GCT | TTG | TAT | CTT | GTT | TAT | 2098 |
| Ala | Ile | Gly | Pro | Leu | Val | Ala | Leu | Tyr | Leu | Val | Tyr | |
| | | | | 545 | | | | | 550 | | | |
| AAA | CAA | GAA | GCC | TCT | ACA | AAA | GCG | GCA | ACA | CCC | ATA | 2134 |
| Lys | Gln | Glu | Ala | Ser | Thr | Lys | Ala | Ala | Thr | Pro | Ile | |
| | | 555 | | | | | 560 | | | | | |
| TGG | CTT | CTG | CTT | TAT | GGT | GGT | GTT | GGC | ATT | TGC | ATG | 2170 |
| Trp | Leu | Leu | Leu | Tyr | Gly | Gly | Val | Gly | Ile | Cys | Met | |
| 565 | | | | 570 | | | | | 575 | | | |
| GGC | CTG | TGG | GTT | TGG | GGA | AGA | AGA | GTT | ATC | CAG | ACC | 2206 |
| Gly | Leu | Trp | Val | Trp | Gly | Arg | Arg | Val | Ile | Gln | Thr | |
| | | | 580 | | | | | 585 | | | | |
| ATG | GGG | AAG | GAC | CTG | ACC | CCA | ATC | ACA | CCC | TCC | AGT | 2242 |
| Met | Gly | Lys | Asp | Leu | Thr | Pro | Ile | Thr | Pro | Ser | Ser | |
| | 590 | | | | | 595 | | | | | 600 | |
| GGT | TTC | AGT | ATT | GAA | CTG | GCG | TCT | GCC | TTA | ACT | GTG | 2278 |
| Gly | Phe | Ser | Ile | Glu | Leu | Ala | Ser | Ala | Leu | Thr | Val | |
| | | | | 605 | | | | | 610 | | | |
| GTC | ATC | GCA | TCA | AAC | ATT | GGC | CTT | CCC | ATC | AGC | ACA | 2314 |
| Val | Ile | Ala | Ser | Asn | Ile | Gly | Leu | Pro | Ile | Ser | Thr | |
| | | 615 | | | | | 620 | | | | | |
| ACA | CAT | TGC | AAA | GTG | GGC | TCT | GTT | GTG | TCT | GTT | GGC | 2350 |
| Thr | His | Cys | Lys | Val | Gly | Ser | Val | Val | Ser | Val | Gly | |
| 625 | | | | 630 | | | | | 635 | | | |
| TGG | CTC | CGA | TCA | AAG | AAG | GCT | GTT | GAC | TGG | CGA | CTG | 2386 |
| Trp | Leu | Arg | Ser | Lys | Lys | Ala | Val | Asp | Trp | Arg | Leu | |
| | | | 640 | | | | | 645 | | | | |
| TTT | CGA | AAC | ATT | TTT | ATG | GCC | TGG | TTT | GTC | ACG | GTC | 2422 |
| Phe | Arg | Asn | Ile | Phe | Met | Ala | Trp | Phe | Val | Thr | Val | |
| | 650 | | | | | 655 | | | | | 660 | |
| CCC | ATC | TCT | GGG | GTT | ATC | AGT | GCC | GCT | ATC | ATG | GCA | 2458 |
| Pro | Ile | Ser | Gly | Val | Ile | Ser | Ala | Ala | Ile | Met | Ala | |
| | | | | 665 | | | | | 670 | | | |
| GTA | TTC | AAG | TAC | ATC | ATC | CTG | CCA | GTG | TGA | | | 2488 |
| Val | Phe | Lys | Tyr | Ile | Ile | Leu | Pro | Val | Xaa | | | |
| | | 675 | | | | | 680 | 681 | | | | |

| | | | |
|---|---|---|---|
| CGCTGGGGTT | GAAAGCTGTG | TCAGTGTCTG | GGACCATTGT | 2528 |
| ACACATTCCT | GTTCCTAGGA | GAACGCTCAC | AGTGTTGCTG | 2568 |
| AAGACAGGCA | AGGGTCTTAA | AGGAGCCGTG | GGAAGGAAGT | 2608 |
| GTAATTTACA | CTATAATTGC | TTTTGTGCTA | AATATGACTT | 2648 |
| ATCTCAAAAT | TAGCTATGTA | AAATAGCCAG | GTTTCCATTG | 2688 |
| ATTCATTCCA | AGGTCCCTTT | TCTCCTGGGC | TATGAATTCC | 2728 |
| TGTACATATT | TCTCTACTTT | TGTATCAGGC | CTCAATTCCA | 2768 |
| GTATGTTTTA | ATGTTGTCTG | TGAGATAACT | TAGGTGGGTT | 2808 |
| CTTTTTAAAC | AGCCAGCAGA | GCCATTTGAT | GGCATGTACT | 2848 |
| GCTTTGTCGG | CCTCACCAGC | TTCTTCCCCA | ACATGCACAG | 2888 |
| GGATTTAACA | ACATGTAACT | GAAGCTTCCC | TCCCTCATAG | 2928 |

| | | | | |
|---|---|---|---|---|
| TCTCTCATAG | AAATAGTCAC | GGCACTCTGC | TCCCTGTCAC | 2968 |
| TAGTGGCAGG | TTCTGTTGAT | GTGTGACAAC | TTCTTAGAGG | 3008 |
| GCCGAGAATC | TTTGGCACAG | TGGAAATATA | AGTTTGTAGT | 3048 |
| AACCTCTTTG | CAAACAGTTC | ACGGACATGT | TGCTAAGAAG | 3088 |
| CAGGGAGACA | AAGCCCCTGG | CGGTTGTGGT | TATTCTTCTG | 3128 |
| AGATTTCTGG | CAGTGTGGGA | TGGGTGAATG | AAGTGGAATG | 3168 |
| TGAACTTTGG | GCAAATTCAA | TGGGACAGCC | TTCCATGTTC | 3208 |
| ATCTGTCTAC | CTCTTAACTG | AATAAAAAGC | CTACAGTTTT | 3248 |
| TAAAAAAAAA | AA | | | 3260 |